United States Patent
Embrey et al.

(10) Patent No.: US 9,951,079 B2
(45) Date of Patent: Apr. 24, 2018

(54) FUSED TRICYCLIC HETEROCYCLIC COMPOUNDS AS HIV INTEGRASE INHIBITORS

(71) Applicant: MERCK SHARP & DOHME CORP., Rahway, NJ (US)

(72) Inventors: Mark W. Embrey, Harleysville, PA (US); Kerim Babaoglu, Lansdale, PA (US); Abbas Walji, Lansdale, PA (US); John S. Wai, Harleysville, PA (US); Paul J. Coleman, Harleysville, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 87 days.

(21) Appl. No.: 14/895,613

(22) PCT Filed: Jun. 9, 2014

(86) PCT No.: PCT/US2014/041464
§ 371 (c)(1),
(2) Date: Dec. 3, 2015

(87) PCT Pub. No.: WO2014/200880
PCT Pub. Date: Dec. 18, 2014

(65) Prior Publication Data
US 2017/0305923 A1  Oct. 26, 2017

Related U.S. Application Data

(60) Provisional application No. 61/834,621, filed on Jun. 13, 2013.

(51) Int. Cl.
| | | |
|---|---|---|
| *C07D 487/14* | (2006.01) | |
| *C07D 498/14* | (2006.01) | |
| *C07D 491/048* | (2006.01) | |
| *A61K 31/5383* | (2006.01) | |
| *A61K 31/4965* | (2006.01) | |
| *A61K 45/06* | (2006.01) | |
| *A61K 31/4985* | (2006.01) | |

(52) U.S. Cl.
CPC ........ *C07D 487/14* (2013.01); *A61K 31/4985* (2013.01); *A61K 31/5383* (2013.01); *A61K 45/06* (2013.01); *C07D 491/048* (2013.01); *C07D 498/14* (2013.01)

(58) Field of Classification Search
None
See application file for complete search history.

(56) References Cited

U.S. PATENT DOCUMENTS

| | | |
|---|---|---|
| 7,037,908 B2 | 5/2006 | Naidu et al. |
| 7,115,601 B2 | 10/2006 | Naidu et al. |
| 7,135,467 B2 | 11/2006 | Walker et al. |
| 7,157,447 B2 | 1/2007 | Naidu et al. |
| 7,169,780 B2 | 1/2007 | Crescenzi et al. |
| 7,173,022 B2 | 2/2007 | Naidu et al. |
| 7,176,196 B2 | 2/2007 | Naidu et al. |
| 7,192,948 B2 | 3/2007 | Banville et al. |
| 7,211,572 B2 | 5/2007 | Miyazaki et al. |
| 7,217,713 B2 | 5/2007 | Crescenzi et al. |
| 7,232,819 B2 | 6/2007 | Di Francesco et al. |
| 7,273,859 B2 | 9/2007 | Naidu |
| 7,414,045 B2 | 8/2008 | Crescenzi et al. |
| 7,419,969 B2 | 9/2008 | Naidu et al. |
| 8,188,271 B2 | 5/2012 | Yoshida et al. |
| 2004/0229909 A1 | 11/2004 | Kiyama et al. |
| 2006/0276466 A1 | 12/2006 | Naidu et al. |
| 2007/0049606 A1 | 3/2007 | Banville et al. |
| 2007/0083045 A1 | 4/2007 | Di Francesco et al. |
| 2007/0111984 A1 | 5/2007 | Naidu et al. |

(Continued)

FOREIGN PATENT DOCUMENTS

| | | |
|---|---|---|
| CA | 2851218 | 4/2014 |
| WO | 2006103399 A1 | 10/2006 |

(Continued)

OTHER PUBLICATIONS

Banker, Gilbert. Modern Pharmaceutics 3rd ed. Marcel Dekker, Inc. New York, (1996).*
MayoClinic. HIV/AIDS. Prevention. (2015) Web. <http://www.mayoclinic.org/diseases-conditions/hiv-aids/basics/prevention/con-20013732>.*
Berge et al., Pharmaceutical Salts, J. Pharm Sci., 1977, pp. 1-19, 66(1).

(Continued)

*Primary Examiner* — Deepak R Rao
*Assistant Examiner* — Laura M Daniel
(74) *Attorney, Agent, or Firm* — Nicole M. Beeler; John C. Todaro

(57) ABSTRACT

The present invention relates to Fused Tricyclic Heterocycle Derivatives of Formula (I): (I) and pharmaceutically acceptable salts thereof, wherein A, X, Y, m, R1, R5, Ra and Rb are as defined herein. The present invention also relates to compositions comprising at least one Fused Tricyclic Heterocycle Derivative, and methods of using the Fused Tricyclic Heterocycle Derivatives for treating or preventing HIV infection in a subject.

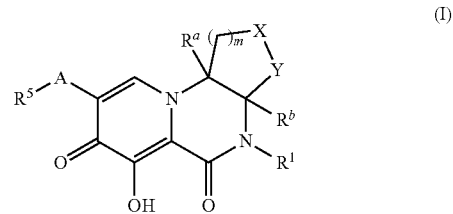

(I)

18 Claims, No Drawings

(56) References Cited

U.S. PATENT DOCUMENTS

| | | |
|---|---|---|
| 2007/0111985 A1 | 5/2007 | Naidu et al. |
| 2007/0112190 A1 | 5/2007 | Naidu |
| 2007/0123524 A1 | 5/2007 | Crescenzi et al. |
| 2007/0142635 A1 | 6/2007 | Askin et al. |
| 2007/0149556 A1 | 6/2007 | Mikamiyama et al. |
| 2008/0004265 A1 | 1/2008 | Walker et al. |
| 2009/0143356 A1 | 6/2009 | Yoshida et al. |
| 2011/0282055 A1 | 11/2011 | Yoshida et al. |
| 2012/0108564 A1 | 5/2012 | Miyazaki et al. |
| 2012/0208998 A1 | 8/2012 | Yoshida et al. |
| 2013/0096109 A1 | 4/2013 | Hattori et al. |

FOREIGN PATENT DOCUMENTS

| | | |
|---|---|---|
| WO | 2011045330 A1 | 4/2011 |
| WO | 2011121105 A1 | 4/2011 |

OTHER PUBLICATIONS

Ester Muraglia, et al, Design and Synthesis of Bicyclic Pyrimidinones as Potent and Orally Bioavailable HIV-1 Integrase Inhibits, J. Med. Chem., 2008, pp. 861-874, vol. 51, US.

Green & Wuts, Protective Groups in Organic Synthesis, 2nd Edition, 1991, -, -.

Hiroyuki Toh, et al, Close Structural Resemblance Between Putative Polymerase of a *Drosophila* Transposable Genetic Element 17.5 and Pol Gene Product of Moloney Murine Leukaemia Virus, The EMBO Journal, 1985, pp. 1267-1272, vol. 4, No. 5, US.

Laurence H. Pearl, et al, A Structural Model for the Retroviral Proteases, Nature, 1987, pp. 351-354, vol. 329, US.

Lee Ratner, et al, Complete Nucleotide Sequence of AIDS Virus, HTLV-III, Nature, 1985, pp. 277-284, vol. 313, US.

Marco Ferrara, et al, Synthesis of a Hexahydropyrimido[1,2-a]Azepine-2-Carboxamide Derivative Useful As an HIV Integrase Inhibitor, Tetrahedron Letters, Jul. 2007, pp. 8379-8382, vol. 48, No. 37, US.

Michael D. Power, et al, Nucleotide Sequence of SSRV-1, a Type D Simian, Science, 1986, pp. 1572, vol. 231.

Olaf D. Kinzel, et al, The Syntheis of Tetrahydropyridopyrimidones As a New Scaffold for HIV-1 Integrase Inhibitors, Tetrahedron Letters, 2007, pp. 6552-6555, vol. 48, No. 37, US.

T. Higuchi and V. Stella, Pro-drugs as NovelDelivery Systems (1987) 14 of the A.C.S. Symposium Series.

The Extended European Search Report for 14811133.9, dated Jan. 17, 2017, 6 pages.

* cited by examiner

FUSED TRICYCLIC HETEROCYCLIC COMPOUNDS AS HIV INTEGRASE INHIBITORS

CROSS-REFERENCE TO RELATED APPLICATIONS

This application is the national stage application under 35 U.S.C. 371 of International Patent Application No. PCT/US2014/041464, filed Jun. 9, 2014, which claims priority to U.S. Provisional Patent Application No. 61/834,621, filed Jun. 13, 2013. Each of the aforementioned applications is incorporated by reference in its entirety.

FIELD OF THE INVENTION

The present invention relates to Fused Tricyclic Heterocycle Derivatives, compositions comprising at least one Fused Tricyclic Heterocycle Derivative, and methods of using the Fused Tricyclic Heterocycle Derivatives for treating or preventing HIV infection in a subject.

BACKGROUND OF THE INVENTION

A retrovirus designated human immunodeficiency virus (HIV), particularly the strains known as HIV type-1 (HIV-1) virus and type-2 (HIV-2) virus, is the etiological agent of the complex disease that includes progressive destruction of the immune system (acquired immune deficiency syndrome; AIDS) and degeneration of the central and peripheral nervous system. A common feature of retrovirus replication is the insertion by virally-encoded integrase of +proviral DNA into the host cell genome, a required step in HIV replication in human T-lymphoid and monocytoid cells. Integration is believed to be mediated by integrase in three steps: assembly of a stable nucleoprotein complex with viral DNA sequences; cleavage of two nucleotides from the 3' termini of the linear proviral DNA; covalent joining of the recessed 3' OH termini of the proviral DNA at a staggered cut made at the host target site. The fourth step in the process, repair synthesis of the resultant gap, may be accomplished by cellular enzymes.

Nucleotide sequencing of HIV shows the presence of a pol gene in one open reading frame [Ratner, L. et al., Nature, 313, 277(1985)]. Amino acid sequence homology provides evidence that the pol sequence encodes reverse transcriptase, integrase and an HIV protease [Toh, H. et al., EMBO J. 4, 1267 (1985); Power, M. D. et al., Science, 231, 1567 (1986); Pearl, L. H. et al., Nature, 329, 351 (1987)]. All three enzymes have been shown to be essential for the replication of HIV.

It is known that some antiviral compounds which act as inhibitors of HIV replication are effective agents in the treatment of AIDS and similar diseases, including reverse transcriptase inhibitors such as azidothymidine (AZT) and efavirenz and protease inhibitors such as indinavir and nelfinavir. The compounds of this invention are inhibitors of HIV integrase and inhibitors of HIV replication.

The following references are of interest as background:

International Publication No. WO 2013/054862 discloses polycyclic pyridone derivatives having HIV integrase inhibitory activity.

US Patent Publication No. US 2012/0208998 discloses polycyclic carbamoylpyridone derivatives having HIV integrase inhibitory activity.

International Publication No. WO 2011/129095 discloses polycyclic pyridone derivatives having HIV integrase inhibitory activity.

International Publication No. WO 2007/049675 discloses polycyclic carbamoylpyridone derivatives having HIV integrase inhibitory activity.

International Publication Nos. WO 11/045330 and WO 11/121105 disclose macrocyclic compounds having HIV integrase inhibitory activity.

Kinzel et al., Tet. Letters 2007, 48(37): pp. 6552-6555 discloses the synthesis of tetrahydropyridopyrimidones as a scaffold for HIV-1 integrase inhibitors.

Ferrara et al., Tet. Letters 2007, 48(37), pp. 8379-8382 discloses the synthesis of a hexahydropyrimido[1,2-a]azepine-2-carboxamide derivative useful as an HIV integrase inhibitor.

Muraglia et al., J. Med. Chem. 2008, 51: 861-874 discloses the design and synthesis of bicyclic pyrimidinones as potent and orally bioavailable HIV-1 integrase inhibitors.

US2004/229909 discloses certain compounds having integrase inhibitory activity.

U.S. Pat. No. 7,232,819 and US 2007/0083045 disclose certain 5,6-dihydroxypyrimidine-4-carboxamides as HIV integrase inhibitors.

U.S. Pat. No. 7,169,780, U.S. Pat. No. 7,217,713, and US 2007/0123524 disclose certain N-substituted 5-hydroxy-6-oxo-1,6-dihydropyrimidine-4-carboxamides as HIV integrase inhibitors.

U.S. Pat. No. 7,279,487 discloses certain hydroxynaphthyridinone carboxamides that are useful as HIV integrase inhibitors.

U.S. Pat. No. 7,135,467 and U.S. Pat. No. 7,037,908 disclose certain pyrimidine carboxamides that are useful as HIV integrase inhibitors.

U.S. Pat. No. 7,211,572 discloses certain nitrogenous condensed ring compounds that are HIV integrase inhibitors.

U.S. Pat. No. 7,414,045 discloses certain tetrahydro-4H-pyrido[1,2-a]pyrimidine carboxamides, hexahydropyrimido[1,2-a]azepine carboxamides, and related compounds that are useful as HIV integrase inhibitors.

WO 2006/103399 discloses certain tetrahydro-4H-pyrimidooxazepine carboxamides, tetrahydropyrazinopyrimidine carboxamides, hexahydropyrimidodiazepine carboxamides, and related compounds that are useful as HIV integrase inhibitors.

US 2007/0142635 discloses processes for preparing hexahydropyrimido[1,2-a]azepine-2-carboxylates and related compounds.

US 2007/0149556 discloses certain hydroxypyrimidinone derivatives having HIV integrase inhibitory activity.

Various pyrimidinone compounds useful as HIV integrase inhibitors are also disclosed in U.S. Pat. No. 7,115,601, U.S. Pat. No. 7,157,447, U.S. Pat. No. 7,173,022, U.S. Pat. No. 7,176,196, U.S. Pat. No. 7,192,948, U.S. Pat. No. 7,273,859, and U.S. Pat. No. 7,419,969.

US 2007/0111984 discloses a series of bicyclic pyrimidinone compounds useful as HIV integrase inhibitors.

US 2006/0276466, US 2007/0049606, US 2007/0111985, US 2007/0112190, US 2007/0281917, US 2008/0004265 each disclose a series of bicyclic pyrimidinone compounds useful as HIV integrase inhibitors.

SUMMARY OF THE INVENTION

In one aspect, the present invention provides Compounds of Formula (I):

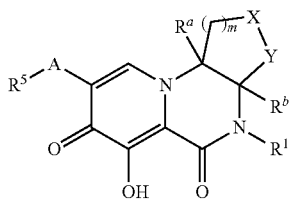

(I)

and pharmaceutically acceptable salts thereof,
wherein:

A is $C_1$-$C_4$ alkylene, $C_2$-$C_4$ alkenylene, $C_3$-$C_7$ cycloalkyl, 5 or 6-membered monocyclic heteroaryl, 4 to 7-membered heterocycloalkyl, arylene, —O—, —NH—C(O)—, —C(O)NH— or —C(O)—;

the group —X—Y— is selected from —O—C($R^2$)$_2$—, —O—C($R^2$)$_2$—C($R^2$)$_2$—, —C($R^2$)$_2$—O—, —N($R^4$)—C($R^2$)$_2$—, —N($R^4$)—C($R^2$)$_2$—C($R^2$)$_2$— and —C($R^2$)$_2$—N($R^4$)—;

m is 1 or 2;

each occurrence of n is independently 0 or 1;

$R^a$ is H or $C_1$-$C_6$ alkyl;

$R^b$ is H or $C_1$-$C_6$ alkyl;

$R^1$ is H or $C_1$-$C_6$ alkyl, which is optionally substituted with up to three $R^3$ groups;

each occurrence of $R^2$ is independently selected from H, $C_1$-$C_6$ alkyl, $C_3$-$C_7$ cycloalkyl, halo, $C_1$-$C_6$ haloalkyl, —C(O)$R^6$, —C(O)N($R^6$)$_2$ and —NHC(O)$R^6$;

each occurrence of $R^3$ is independently selected from $C_3$-$C_7$ cycloalkyl, 5 or 6-membered monocyclic heteroaryl, 4 to 6-membered monocyclic heterocycloalkyl, $C_6$-$C_{10}$ aryl, halo, $C_1$-$C_6$ haloalkyl, —O$R^6$, —N($R^6$)$_2$, —C(O)$R^6$, —C(O)N($R^6$)$_2$, —NHC(O)$R^6$ and —S$R^6$, wherein said $C_3$-$C_7$ cycloalkyl group, said 5 or 6-membered monocyclic heteroaryl group, said 4 to 6-membered monocyclic heterocycloalkyl group and said $C_6$-$C_{10}$ aryl group can each be optionally and independently substituted with one or more groups, each independently selected from $C_1$-$C_6$ alkyl, $C_3$-$C_7$ cycloalkyl, 5 or 6-membered monocyclic heteroaryl, 4 to 6-membered monocyclic heterocycloalkyl, $C_6$-$C_{10}$ aryl, halo, $C_1$-$C_6$ haloalkyl, —O$R^6$, —N($R^6$)$_2$, —C(O)$R^6$, —C(O)O$R^6$, —C(O)N($R^6$)$_2$, —NHC(O)$R^6$ and —S$R^6$;

$R^4$ is $C_1$-$C_6$ alkyl, $C_3$-$C_7$ cycloalkyl or $C_6$-$C_{10}$ aryl, wherein said $C_3$-$C_7$ cycloalkyl group and said $C_6$-$C_{10}$ aryl group can be optionally substituted with one or more groups, each independently selected from $C_1$-$C_6$ alkyl, $C_3$-$C_7$ cycloalkyl, $C_6$-$C_{10}$ aryl, halo, $C_1$-$C_6$ haloalkyl, —C(O)$R^6$, —C(O)O$R^6$, —C(O)N($R^6$)$_2$, —NHC(O)$R^6$ and —S(O)$_2R^6$;

$R^5$ is selected from $C_1$-$C_6$ alkyl, —($C_1$-$C_3$ alkylene)$_n$-($C_3$-$C_7$ cycloalkyl), —($C_1$-$C_3$ alkylene)$_n$-(5 or 6-membered monocyclic heteroaryl), —($C_1$-$C_3$ alkylene)$_n$-(4 to 6-membered monocyclic heterocycloalkyl) and —($C_1$-$C_3$ alkylene)$_n$-($C_6$-$C_{10}$ aryl), wherein said $C_3$-$C_7$ cycloalkyl group, said 5 or 6-membered monocyclic heteroaryl group, said 4 to 6-membered monocyclic heterocycloalkyl group and said $C_6$-$C_{10}$ aryl group can each be optionally and independently substituted with one or more groups, each independently selected from $C_1$-$C_6$ alkyl, $C_3$-$C_7$ cycloalkyl, 5 or 6-membered monocyclic heteroaryl, 4 to 6-membered monocyclic heterocycloalkyl, $C_6$-$C_{10}$ aryl, halo, $C_1$-$C_6$ haloalkyl, —O$R^6$, —N($R^6$)$_2$, —C(O)$R^6$, —C(O)N($R^6$)$_2$, —NHC(O)$R^6$, —S(O)$_2R^6$ and —S$R^6$; and each occurrence of $R^6$ is independently selected from H, $C_1$-$C_6$ alkyl, $C_3$-$C_7$ cycloalkyl, $C_6$-$C_{10}$ aryl and benzyl.

The Compounds of Formula (I) (also referred to herein as the "Fused Tricyclic Heterocycle Derivatives") and pharmaceutically acceptable salts thereof can be useful, for example, for inhibiting HIV viral replication or replicon activity, and for treating or preventing HIV infection in a subject. Without being bound by any specific theory, it is believed that the Fused Tricyclic Heterocycle Derivatives inhibit HIV viral replication by inhibiting HIV Integrase.

Accordingly, the present invention provides methods for treating or preventing HIV infection in a subject, comprising administering to the subject an effective amount of at least one Fused Tricyclic Heterocycle Derivative.

The details of the invention are set forth in the accompanying detailed description below.

Although any methods and materials similar to those described herein can be used in the practice or testing of the present invention, illustrative methods and materials are now described. Other embodiments, aspects and features of the present invention are either further described in or will be apparent from the ensuing description, examples and appended claims.

DETAILED DESCRIPTION OF THE INVENTION

The present invention relates to Fused Tricyclic Heterocycle Derivatives, compositions comprising at least one Fused Tricyclic Heterocycle Derivative, and methods of using the Fused Tricyclic Heterocycle Derivatives for inhibiting HIV integrase, inhibiting HIV viral replication or for treating or preventing HIV infection in a subject.

Definitions and Abbreviations

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc. . . . .

As used herein, and throughout this disclosure, the following terms, unless otherwise indicated, shall be understood to have the following meanings:

A "subject" is a human or non-human mammal. In one embodiment, a subject is a human. In another embodiment, a subject is a primate. In another embodiment, a subject is a monkey. In another embodiment, a subject is a chimpanzee. In still another embodiment, a subject is a rhesus monkey.

The term "effective amount" as used herein, refers to an amount of Fused Tricyclic Heterocycle Derivative and/or an additional therapeutic agent, or a composition thereof that is effective in producing the desired therapeutic, ameliorative, inhibitory or preventative effect when administered to a subject suffering from HIV infection or AIDS. In the combination therapies of the present invention, an effective amount can refer to each individual agent or to the combination as a whole, wherein the amounts of all agents administered are together effective, but wherein the component agent of the combination may not be present individually in an effective amount.

The term "preventing," as used herein with respect to an HIV viral infection or AIDS, refers to reducing the likelihood or severity of HIV infection or AIDS.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl) or from about 1 to about 4 carbon atoms ($C_1$-$C_4$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or substituted by one or more substituents which may be the same or different. Illustrative examples of substituents include, but are not limited to, halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, an alkyl group is linear. In another embodiment, an alkyl group is branched. Unless otherwise indicated, an alkyl group is unsubstituted.

The term "alkenyl," as used herein, refers to an aliphatic hydrocarbon group containing at least one carbon-carbon double bond and having one of its hydrogen atoms replaced with a bond. An alkenyl group may be straight or branched and contain from about 2 to about 15 carbon atoms. In one embodiment, an alkenyl group contains from about 2 to about 12 carbon atoms. In another embodiment, an alkenyl group contains from about 2 to about 6 carbon atoms. Non-limiting examples of alkenyl groups include ethenyl, propenyl, n-butenyl, 3-methylbut-2-enyl, n-pentenyl, octenyl and decenyl. An alkenyl group may be unsubstituted or substituted by one or more substituents which may be the same or different. Illustrative examples of substituents include, but are not limited to, halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "$C_2$-$C_6$ alkenyl" refers to an alkenyl group having from 2 to 6 carbon atoms. Unless otherwise indicated, an alkenyl group is unsubstituted.

The term "alkynyl," as used herein, refers to an aliphatic hydrocarbon group containing at least one carbon-carbon triple bond and having one of its hydrogen atoms replaced with a bond. An alkynyl group may be straight or branched and contain from about 2 to about 15 carbon atoms. In one embodiment, an alkynyl group contains from about 2 to about 12 carbon atoms. In another embodiment, an alkynyl group contains from about 2 to about 6 carbon atoms. Non-limiting examples of alkynyl groups include ethynyl, propynyl, 2-butynyl and 3-methylbutynyl. An alkynyl group may be unsubstituted or substituted by one or more substituents which may be the same or different. Illustrative examples of substituents include, but are not limited to, halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "$C_2$-$C_6$ alkynyl" refers to an alkynyl group having from 2 to 6 carbon atoms. Unless otherwise indicated, an alkynyl group is unsubstituted.

The term "alkylene," as used herein, refers to an alkyl group, as defined above, wherein one of the alkyl group's hydrogen atoms has been replaced with a bond. Non-limiting examples of alkylene groups include —$CH_2$—, —$CH_2CH_2$—, —$CH_2CH_2CH_2$—, —$CH_2CH_2CH_2CH_2$—, —CH($CH_3$)$CH_2CH_2$—, —CH($CH_3$)— and —$CH_2$CH($CH_3$)$CH_2$—. In one embodiment, an alkylene group has from 1 to about 6 carbon atoms. In another embodiment, an alkylene group has from about 3 to about 5 carbon atoms. In another embodiment, an alkylene group is branched. In another embodiment, an alkylene group is linear. In one embodiment, an alkylene group is —$CH_2$—. The term "$C_1$-$C_6$ alkylene" refers to an alkylene group having from 1 to 6 carbon atoms. The term "$C_3$-$C_5$ alkylene" refers to an alkylene group having from 3 to 5 carbon atoms.

The term "alkenylene," as used herein, refers to an alkenyl group, as defined above, wherein one of the alkenyl group's hydrogen atoms has been replaced with a bond. Non-limiting examples of alkenylene groups include —CH=CH—, —CH=CHCH$_2$—, —CH$_2$CH=CH—, —CH$_2$CH=CHCH$_2$—, —CH=CHCH$_2$CH$_2$—, —CH$_2$CH$_2$CH=CH— and —CH(CH$_3$)CH=CH—. In one embodiment, an alkenylene group has from 2 to about 6 carbon atoms. In another embodiment, an alkenylene group has from about 2 to about 4 carbon atoms. In another embodiment, an alkenylene group is branched. In another embodiment, an alkenylene group is linear. The term "$C_2$-$C_6$ alkylene" refers to an alkenylene group having from 2 to 6 carbon atoms. The term "$C_2$-$C_4$ alkenylene" refers to an alkylene group having from 2 to 4 carbon atoms.

The term "aryl," as used herein, refers to an aromatic monocyclic or multicyclic ring system comprising from about 6 to about 14 carbon atoms. In one embodiment, an aryl group contains from about 6 to about 10 carbon atoms. An aryl group can be optionally substituted with one or more "ring system substituents" which may be the same or different, and are as defined herein below. In one embodiment, an aryl group can be optionally fused to a cycloalkyl or cycloalkanoyl group. Non-limiting examples of aryl groups include phenyl and naphthyl. In one embodiment, an aryl group is phenyl. Unless otherwise indicated, an aryl group is unsubstituted.

The term "arylene," as used herein, refers to a bivalent group derived from an aryl group, as defined above, by removal of a hydrogen atom from a ring carbon of an aryl group. An arylene group can be derived from a monocyclic or multicyclic ring system comprising from about 6 to about 14 carbon atoms. In one embodiment, an arylene group contains from about 6 to about 10 carbon atoms. In another embodiment, an arylene group is a naphthylene group. In another embodiment, an arylene group is a phenylene group. An arylene group can be optionally substituted with one or more "ring system substituents" which may be the same or different, and are as defined herein below. An arylene group is divalent and either available bond on an arylene group can connect to either group flanking the arylene group. For example, the group "A-arylene-B," wherein the arylene group is:

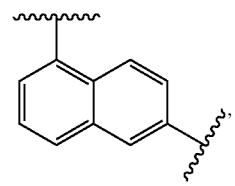 [SMILES: *c1ccc2c(*)cccc2c1]

is understood to represent both:

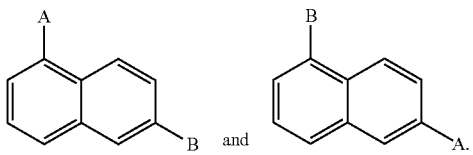

In one embodiment, an arylene group can be optionally fused to a cycloalkyl or cycloalkanoyl group. Non-limiting examples of arylene groups include phenylene and naphthalene. In one embodiment, an arylene group is unsubstituted. In another embodiment, an arylene group is:

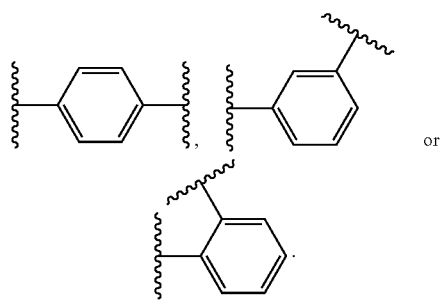

Unless otherwise indicated, an arylene group is unsubstituted.

The term "cycloalkyl," as used herein, refers to a non-aromatic mono- or multicyclic ring system comprising from about 3 to about 10 ring carbon atoms. In one embodiment, a cycloalkyl contains from about 5 to about 10 ring carbon atoms. In another embodiment, a cycloalkyl contains from about 3 to about 7 ring atoms. In another embodiment, a cycloalkyl contains from about 5 to about 6 ring atoms. The term "cycloalkyl" also encompasses a cycloalkyl group, as defined above, which is fused to an aryl (e.g., benzene) or heteroaryl ring. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl. A cycloalkyl group can be optionally substituted with one or more "ring system substituents" which may be the same or different, and are as defined herein below. In one embodiment, a cycloalkyl group is unsubstituted. The term "3 to 7-membered cycloalkyl" refers to a cycloalkyl group having from 3 to 7 ring carbon atoms. Unless otherwise indicated, a cycloalkyl group is unsubstituted. A ring carbon atom of a cycloalkyl group may be functionalized as a carbonyl group. An illustrative example of such a cycloalkyl group (also referred to herein as a "cycloalkanoyl" group) includes, but is not limited to, cyclobutanoyl:

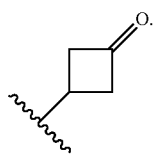 [SMILES: *C1CC(=O)C1]

The term "halo," as used herein, means —F, —Cl, —Br or —I.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —$CH_2F$, —$CHF_2$, —$CF_3$, —$CH_2Cl$ and —$CCl_3$. The term "$C_1$-$C_6$ haloalkyl" refers to a haloalkyl group having from 1 to 6 carbon atoms.

The term "hydroxyalkyl," as used herein, refers to an alkyl group as defined above, wherein one or more of the alkyl group's hydrogen atoms have been replaced with an —OH group. In one embodiment, a hydroxyalkyl group has from 1 to 6 carbon atoms. Non-limiting examples of hydroxyalkyl groups include —$CH_2OH$, —$CH_2CH_2OH$, —$CH_2CH_2CH_2OH$ and —$CH_2CH(OH)CH_3$. The term "$C_1$-$C_6$ hydroxyalkyl" refers to a hydroxyalkyl group having from 1 to 6 carbon atoms.

The term "heteroaryl," as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is bicyclic. A heteroaryl group can be optionally substituted by one or more "ring system substituents" which may be the same or different, and are as defined herein below. A heteroaryl group is joined via a ring carbon atom, and any nitrogen atom of a heteroaryl can be optionally oxidized to the corresponding N-oxide. The term "heteroaryl" also encompasses a heteroaryl group, as defined above, which is fused to a benzene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,3,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, benzimidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like, and all isomeric forms thereof. The term "heteroaryl" also refers to partially saturated heteroaryl moieties such as, for example, tetrahydroisoquinolyl, tetrahydroquinolyl and the like. In one embodiment, a heteroaryl group is a 5-membered heteroaryl. In another embodiment, a heteroaryl group is a 6-membered monocyclic heteroaryl. In another embodiment, a heteroaryl group comprises a 5- to 6-membered monocyclic heteroaryl group fused to a benzene ring. Unless otherwise indicated, a heteroaryl group is unsubstituted.

The term "heterocycloalkyl," as used herein, refers to a non-aromatic saturated monocyclic or multicyclic ring system comprising 3 to about 11 ring atoms, wherein from 1 to 4 of the ring atoms are independently O, S, N or Si, and the remainder of the ring atoms are carbon atoms. A heterocycloalkyl group can be joined via a ring carbon, ring silicon atom or ring nitrogen atom. In one embodiment, a heterocycloalkyl group is monocyclic and has from about 3 to about 7 ring atoms. In another embodiment, a heterocycloalkyl group is monocyclic has from about 4 to about 7 ring atoms. In another embodiment, a heterocycloalkyl group is bicyclic and has from about 7 to about 11 ring atoms. In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. The term "heterocycloalkyl" also encompasses a heterocycloalkyl group, as defined above, which is fused to an aryl (e.g., benzene) or heteroaryl ring. A heterocycloalkyl group can be optionally substituted by one or more "ring system substituents" which may be the same or different, and are as defined herein below. The nitrogen or sulfur atom of the heterocycloalkyl can be optionally oxidized to the corresponding N-oxide, S-oxide or S,S-dioxide. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, pyranyl, tetrahydrothiophenyl, delta-lactam, delta-lactone and the like, and all isomers thereof.

A ring carbon atom of a heterocycloalkyl group may be functionalized as a carbonyl group. An illustrative example of such a heterocycloalkyl group is:

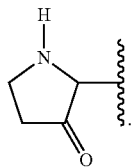

In one embodiment, a heterocycloalkyl group is a 5-membered monocyclic heterocycloalkyl. In another embodiment, a heterocycloalkyl group is a 6-membered monocyclic heterocycloalkyl. The term "3 to 6-membered monocyclic heterocycloalkyl" refers to a monocyclic heterocycloalkyl group having from 3 to 6 ring atoms. The term "4 to 7-membered monocyclic heterocycloalkyl" refers to a monocyclic heterocycloalkyl group having from 4 to 7 ring atoms. The term "7 to 11-membered bicyclic heterocycloalkyl" refers to a bicyclic heterocycloalkyl group having from 7 to 11 ring atoms. Unless otherwise indicated, a heterocycloalkyl group is unsubstituted.

The term "ring system substituent," as used herein, refers to a substituent group attached to an aromatic or non-aromatic ring system which, for example, replaces an available hydrogen on the ring system. Ring system substituents may be the same or different. Illustrative examples of ring system substituents include, but are not limited to, alkyl, alkenyl, alkynyl, aryl, heteroaryl, -alkylene-aryl, -arylene-alkyl, -alkylene-heteroaryl, -alkenylene-heteroaryl, -alkynylene-heteroaryl, —OH, hydroxyalkyl, haloalkyl, —O-alkyl, —O-haloalkyl, -alkylene-O-alkyl, —O-aryl, —O-alkylene-aryl, acyl, —C(O)-aryl, halo, —NO$_2$, —CN, —SF$_5$, —C(O)OH, —C(O)O-alkyl, —C(O)O-aryl, —C(O)O-alkylene-aryl, —S(O)-alkyl, —S(O)$_2$-alkyl, —S(O)-aryl, —S(O)$_2$-aryl, —S(O)-heteroaryl, —S(O)$_2$-heteroaryl, —S-alkyl, —S-aryl, —S-heteroaryl, —S-alkylene-aryl, —S-alkylene-heteroaryl, —S(O)$_2$-alkylene-aryl, —S(O)$_2$-alkylene-heteroaryl, —Si(alkyl)$_2$, —Si(aryl)$_2$, —Si(heteroaryl)$_2$, —Si(alkyl)(aryl), —Si(alkyl)(cycloalkyl), —Si (alkyl)(heteroaryl), cycloalkyl, heterocycloalkyl, —O—C (O)-alkyl, —O—C(O)-aryl, —O—C(O)-cycloalkyl, —C(=N—CN)—NH$_2$, —C(=NH)—NH$_2$, —C(=NH)—NH(alkyl), —N(Y$_1$)(Y$_2$), -alkylene-N(Y$_1$)(Y$_2$), —C(O)N (Y$_1$)(Y$_2$) and —S(O)$_2$N(Y$_1$)(Y$_2$), wherein Y$_1$ and Y$_2$ can be the same or different and are independently selected from the group consisting of hydrogen, alkyl, aryl, cycloalkyl, and -alkylene-aryl. "Ring system substituent" may also mean a single moiety which simultaneously replaces two available hydrogens on two adjacent carbon atoms (one H on each carbon) on a ring system. Examples of such moiety are methylenedioxy, ethylenedioxy, —C(CH$_3$)$_2$— and the like which form moieties such as, for example:

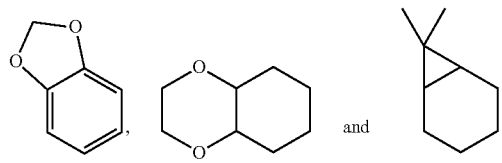

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any substituent or variable (e.g., alkyl, R$^1$, R$^7$, etc.) occurs more than one time in any constituent or in Formula (I), its definition on each occurrence is independent of its definition at every other occurrence, unless otherwise indicated.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to provide a Fused Tricyclic Heterocycle Derivative or a pharmaceutically acceptable salt of the compound. The transformation may occur by various mechanisms (e.g., by metabolic or chemical processes), such as, for example, through hydrolysis in blood. For example, if a Fused Tricyclic Heterocycle Derivative or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di $(C_1-C_2)$alkylcarbamoyl-$(C_1-C_2)$alkyl and piperidino-, pyrrolidino- or morpholino$(C_2-C_3)$alkyl, and the like.

Similarly, if a Fused Tricyclic Heterocycle Derivative contains an alcohol functional group, a prodrug can be formed by the replacement of one or more of the hydrogen atoms of the alcohol groups with a group such as, for example, $(C_1-C_6)$alkanoyloxymethyl, 1-(($C_1-C_6$)alkanoyloxy)ethyl, 1-methyl-1-(($C_1-C_6$)alkanoyloxy)ethyl, $(C_1-C_6)$ alkoxycarbonyloxymethyl, N—$(C_1-C_6)$alkoxycarbonylaminomethyl, succinoyl, $(C_1-C_6)$alkanoyl, α-amino$(C_1-C_4)$ alkyl, α-amino$(C_1-C_4)$alkylene-aryl, arylacyl and α-aminoacyl, or α-aminoacyl-α-aminoacyl, where each α-aminoacyl group is independently selected from the naturally occurring L-amino acids, or glycosyl (the radical resulting from the removal of a hydroxyl group of the hemiacetal form of a carbohydrate).

If a Fused Tricyclic Heterocycle Derivative incorporates an amine functional group, a prodrug can be formed by the replacement of a hydrogen atom in the amine group with a group such as, for example, R-carbonyl-, RO-carbonyl-, NRR'-carbonyl- wherein R and R' are each independently $(C_1-C_{10})$alkyl, $(C_3-C_7)$ cycloalkyl, benzyl, a natural α-aminoacyl, —C(OH)C(O)OY$^1$ wherein Y$^1$ is H, $(C_1-C_6)$ alkyl or benzyl, —C(OY$^2$)Y$^3$ wherein Y$^2$ is $(C_1-C_4)$ alkyl and Y$^3$ is $(C_1-C_6)$alkyl; carboxy $(C_1-C_6)$alkyl; amino$(C_1-C_4)$alkyl or mono-N- or di-N,N—$(C_1-C_6)$alkylaminoalkyl; —C(Y$^4$)Y$^5$ wherein Y$^4$ is H or methyl and Y$^5$ is mono-N- or di-N,N—$(C_1-C_6)$alkylamino morpholino; piperidin-1-yl or pyrrolidin-1-yl, and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (e.g., methyl, ethyl, n-propyl, isopropyl, t-butyl, sec-butyl or n-butyl), alkoxyalkyl (e.g., methoxymethyl), aralkyl (e.g., benzyl), aryloxyalkyl (for example, phenoxymethyl), aryl (e.g., phenyl optionally substituted with, for example, halogen, $C_{1-4}$alkyl, —O—$(C_{1-4}$alkyl) or amino); (2) sulfonate esters, such as alkyl- or aralkylsulfonyl (for example, methanesulfonyl); (3) amino acid esters, including those corresponding to both natural and non-natural amino acids (e.g., L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di $(C_{6-24})$acyl glycerol.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. A "hydrate" is a solvate wherein the solvent molecule is water.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTechours.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than room temperature, and cooling the solution at a rate sufficient to form crystals which are then isolated by standard methods. Analytical techniques such as, for example IR spectroscopy, show the presence of the solvent (or water) in the crystals as a solvate (or hydrate).

The Fused Tricyclic Heterocycle Derivatives can form salts which are also within the scope of this invention. Reference to a Fused Tricyclic Heterocycle Derivative herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a Fused Tricyclic Heterocycle Derivative contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the Compounds of Formula (I) may be formed, for example, by reacting a Fused Tricyclic Heterocycle Derivative with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Diastereomeric mixtures can be separated into their individual diastereomers on the basis of their physical chemical differences by methods well-known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Sterochemically pure compounds may also be prepared by using chiral starting materials or by employing salt resolution techniques. Also, some of the Fused Tricyclic Heterocycle Derivatives may be atropisomers (e.g., substituted biaryls) and are considered as part of this invention. Enantiomers can also be directly separated using chiral chromatographic techniques.

It is also possible that the Fused Tricyclic Heterocycle Derivatives may exist in different tautomeric forms, and all such forms are embraced within the scope of the invention. For example, all keto-enol and imine-enamine forms of the compounds are included in the invention.

All stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. If a Fused Tricyclic Heterocycle Derivative incorporates a double bond or a fused ring, both the cis- and trans-forms, as well as mixtures, are embraced within the scope of the invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to apply equally to the salt, solvate, ester and prodrug of enantiomers, stereoisomers, rotamers, tautomers, racemates or prodrugs of the inventive compounds.

In the Compounds of Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched Compounds of Formula (I) can be prepared without undue experimentation by conventional techniques well known to those skilled in the art or by processes analogous to those described in the Schemes and Examples herein using appropriate isotopically-enriched reagents and/or intermediates. In one embodiment, a Compound of Formula (I) has one or more of its hydrogen atoms replaced with deuterium.

Polymorphic forms of the Fused Tricyclic Heterocycle Derivatives, and of the salts, solvates, hydrates, esters and prodrugs of the Fused Tricyclic Heterocycle Derivatives, are intended to be included in the present invention.

GENERAL LIST OF ABBREVIATIONS

AcOH=acetic acid
Alk=alkyl
Ar=aryl
Boc=tert-butoxycarbonyl
BOP=(benzotriazol-1-yl)oxy)tris(dimethylamino)phosphonium hexafluorophosphate
br=broad
n-BuOH=N-butanol
C=Celsius
d=doublet
dd=doublet of doublets
dt=doublet of triplets
DCM=dichloromethane
DEA=N,N-diethylamine
DIEA=N,N-diisopropylethylamine
DMA=N,N-dimethylacetamide
DMF=dimethylformamide
DMSO=dimethyl sulfoxide
EDC=1-ethyl-3-(3'-dimethylaminopropyl)carbodiimide hydrochloride
ESI=electrospray ionization
EtOAc=ethyl acetate
EtOH=ethanol
HATU=2-(1H-7-Azabenzotriazol-1-yl)-1,1,3,3-tetramethyl uronium hexafluorophosphate
HOAt=1-hydroxy-7-azabenzotriazole
HOBt=1-hydroxybenzotriazole
HRMS=high resolution mass spectrometry LCMS=liquid chromatography/mass spectrometry
LiHMDS=lithium bis(trimethylsilyl)amide
LRMS=low resolution mass spectrometry
m=multiplet
min=minutes
MS=mass spectroscopy
MTBE=methyl tert-butyl ether
NBS=N-bromosuccinimide
NIS=N-iodosuccinimide
NMR=nuclear magnetic resonance spectroscopy
PE=petroleum ether
Piv=pivalate, 2,2-dimethylpropanoyl
Ph=phenyl
s=singlet
SFC=supercritical fluid chromatography
t=triplet
TEA=triethylamine
TFA=trifluoroacetic acid
THF=tetrahydrofuran
TLC=thin-layer chromatography
wt %=weight percent The Compounds of Formula (I)

The present invention provides Fused Tricyclic Heterocycle Derivatives of Formula (I):

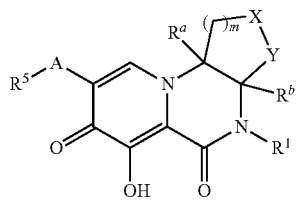
(I)

and pharmaceutically acceptable salts thereof, wherein A, X, Y, m, $R^1$, $R^5$, $R^a$ and $R^b$ are as defined above for the Compounds of Formula (I).

In one embodiment, A is 5 or 6-membered monocyclic heteroaryl or —NH—C(O)—.

In one embodiment, the group X—Y— is selected from —O—CH$_2$—, —O—CH$_2$—CH$_2$— and —CH$_2$—O—.

In one embodiment, $R^a$ is H.

In another embodiment, $R^b$ is H.

In another embodiment, $R^a$ and $R^b$ are each H.

In one embodiment, $R^5$ is —(C$_1$-C$_3$ alkylene)$_n$-(C$_6$-C$_{10}$ aryl), wherein the C$_6$-C$_{10}$ aryl moiety of said —(C$_1$-C$_3$ alkylene)$_n$-(C$_6$-C$_{10}$ aryl) group can be can be optionally and independently substituted as set forth above for the compounds of formula (I).

In another embodiment, $R^5$ is benzyl, wherein the phenyl moiety of said benzyl group can be can be optionally and independently substituted with up to 3 groups, each independently selected from F and methyl.

In another embodiment, $R^5$ is:

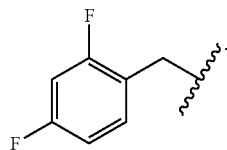

In one embodiment, the Compounds of Formula (I) have Formula (Ia):

2.

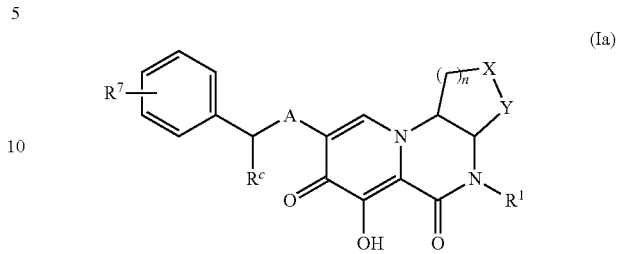
(Ia)

and pharmaceutically acceptable salts thereof,
wherein:
A is —NH—C(O)— or 5-membered heteroaryl;
the group —X—Y— is selected from —O—CH$_2$—, —O—CH$_2$—CH$_2$— and —CH$_2$—O—.
n is 1 or 2;
$R^1$ is H or C$_1$-C$_6$ alkyl;
$R^7$ represents up to 2 phenyl group substituents, each independently selected from halo; and
$R^c$ is H or C$_1$-C$_6$ alkyl.

In one embodiment, for the compounds of formula (Ia), $R^c$ is H.

In another embodiment, for the compounds of formula (Ia), $R^c$ is C$_1$-C$_6$ alkyl.

In another embodiment, for the compounds of formula (Ia), $R^c$ is ethyl.

In one embodiment, for the compounds of formula (Ia), each occurrence of $R^7$ is F.

In one embodiment, for the compounds of formula (Ia), $R^7$ represents two F substitutents, located at the ortho and para positions on the phenyl group to which they are attached.

In one embodiment, for the compounds of formula (I) or (Ia), A is 5-membered monocyclic heteroaryl.

In another embodiment, for the compounds of formula (I) or (Ia), A is —NHC(O)—, thiadiazolyl, triazolyl or pyrazoyl.

In another embodiment, for the compounds of formula (I) or (Ia), A is —NHC(O)—,

In still another embodiment, for the compounds of formula (I) or (Ia), A is thiadiazolyl.

In another embodiment, for the compounds of formula (I) or (Ia), A is triazolyl.

In another embodiment, for the compounds of formula (I) or (Ia), A is pyrazoyl.

In one embodiment, for the compounds of formula (I) or (Ia), the group —X—Y— is —O—CH$_2$—.

In another embodiment, for the compounds of formula (I) or (Ia), the group —X—Y— is —O—CH$_2$—CH$_2$—

In another embodiment, for the compounds of formula (I) or (Ia), the group —X—Y— is —CH$_2$—O—.

In one embodiment, for the compounds of formula (I) or (Ia), n is 1.

In another embodiment, for the compounds of formula (I) or (Ia), n is 2.

In one embodiment, for the compounds of formula (I) or (Ia), n is 1 and the group X—Y— is —O—CH$_2$—.

In another embodiment, for the compounds of formula (I) or (Ia), $R^1$ is H, ethyl, isopropyl, n-propyl or —CH$_2$CH$_2$OCH$_3$.

In another embodiment, for the compounds of formula (I) or (Ia), $R^1$ is ethyl or —CH$_2$CH$_2$OCH$_3$.

In another embodiment, for the compounds of formula (I) or (Ia), $R^1$ is $C_1$-$C_6$ alkyl.

In still another embodiment, for the compounds of formula (I) or (Ia), $R^1$ is ethyl.

In another embodiment, for the compounds of formula (I) or (Ia), $R^1$ is isopropyl.

In another embodiment, for the compounds of formula (I) or (Ia), $R^1$ is H.

In one embodiment, $R^5$ is benzyl, wherein the phenyl moiety of said benzyl group can be can be optionally and independently substituted with up to 3 groups, each independently selected from —$OR^6$, $C_1$-$C_6$ alkyl and halo.

In one embodiment, variables A, X, Y, m, $R^1$, $R^5$, $R^a$ and $R^b$ for the Compounds of Formula (I) are selected independently of each other.

In another embodiment, the Compounds of Formula (I) are in substantially purified form.

Other embodiments of the present invention include the following:

(a) A pharmaceutical composition comprising an effective amount of a Compound of Formula (I) or a pharmaceutically acceptable salt thereof, and a pharmaceutically acceptable carrier.

(b) The pharmaceutical composition of (a), further comprising a second therapeutic agent selected from the group consisting of HIV antiviral agents, immunomodulators, and anti-infective agents.

(c) The pharmaceutical composition of (b), wherein the HIV antiviral agent is an antiviral selected from the group consisting of HIV protease inhibitors, HIV integrase inhibitors, nucleoside reverse transcriptase inhibitors, CCR5 co-receptor antagonists and non-nucleoside reverse-transcriptase inhibitors.

(d) A pharmaceutical combination that is (i) a Compound of Formula (I) and (ii) a second therapeutic agent selected from the group consisting of HIV antiviral agents, immunomodulators, and anti-infective agents; wherein the Compound of Formula (I) and the second therapeutic agent are each employed in an amount that renders the combination effective for inhibiting HIV replication, or for treating HIV infection and/or reducing the likelihood or severity of symptoms of HIV infection.

(e) The combination of (d), wherein the HIV antiviral agent is an antiviral selected from the group consisting of HIV protease inhibitors, nucleoside reverse transcriptase inhibitors, CCR5 co-receptor antagonists, fusion and non-nucleoside reverse-transcriptase inhibitors.

(f) A method of inhibiting HIV replication in a subject in need thereof which comprises administering to the subject an effective amount of a Compound of Formula (I).

(g) A method of treating HIV infection and/or reducing the likelihood or severity of symptoms of HIV infection in a subject in need thereof which comprises administering to the subject an effective amount of a Compound of Formula (I).

(h) The method of (g), wherein the Compound of Formula (I) is administered in combination with an effective amount of at least one second therapeutic agent selected from the group consisting of HIV antiviral agents, immunomodulators, and anti-infective agents.

(i) The method of (h), wherein the HIV antiviral agent is an antiviral selected from the group consisting of HIV protease inhibitors, nucleoside reverse transcriptase inhibitors, CCR5 co-receptor antagonists, fusion and non-nucleoside reverse-transcriptase inhibitors.

(j) A method of inhibiting HIV replication in a subject in need thereof which comprises administering to the subject the pharmaceutical composition of (a), (b) or (c) or the combination of (d) or (e).

(k) A method of treating HIV infection and/or reducing the likelihood or severity of symptoms of HIV infection in a subject in need thereof which comprises administering to the subject the pharmaceutical composition of (a), (b) or (c) or the combination of (d) or (e).

The present invention also includes a compound of the present invention for use (i) in, (ii) as a medicament for, or (iii) in the preparation of a medicament for: (a) medicine, (b) inhibiting HIV replication or (c) treating HIV infection and/or reducing the likelihood or severity of symptoms of HIV infection. In these uses, the compounds of the present invention can optionally be employed in combination with one or more second therapeutic agents selected from HIV antiviral agents, anti-infective agents, and immunomodulators.

Additional embodiments of the invention include the pharmaceutical compositions, combinations and methods set forth in (a)-(k) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate. It is understood that references to compounds would include the compound in its present form as well as in different forms, such as polymorphs, solvates and hydrates, as applicable.

It is further to be understood that the embodiments of compositions and methods provided as (a) through (k) above are understood to include all embodiments of the compounds, including such embodiments as result from combinations of embodiments.

The Compounds of Formula (I) may be referred to herein by chemical structure and/or by chemical name. In the instance that both the structure and the name of a Compound of Formula (I) are provided and a discrepancy is found to exist between the chemical structure and the corresponding chemical name, it is understood that the chemical structure will predominate.

Non-limiting examples of the Compounds of Formula (I) include compounds 1-16 as set forth below, and pharmaceutically acceptable salts thereof.

Methods for Making the Compounds of Formula (I)

The Compounds of Formula (I) may be prepared from known or readily prepared starting materials, following methods known to one skilled in the art of organic synthesis. Methods useful for making the Compounds of Formula (I) are set forth in the Examples below and generalized in Schemes A-D, below. Alternative synthetic pathways and analogous structures will be apparent to those skilled in the art of organic synthesis. Unless otherwise indicated, all variables are as defined above.

Scheme A depicts a general method for preparing compounds of the present invention wherein a cyclic diamine 2 is condensed into a pyranone 1 to provide the intermediate pyridinone, which then cyclizes to form the lactam 3. This reaction may need in-situ protection of one of the amines by the addition of benzaldehyde followed later by in-situ deprotection with water. The lactam is then alkylated to provide 4.

The same conditions can also provide compounds with branching off of the benzylic position as shown. Deprotection affords the representative HIV integrase inhibitor 5 of the present invention.

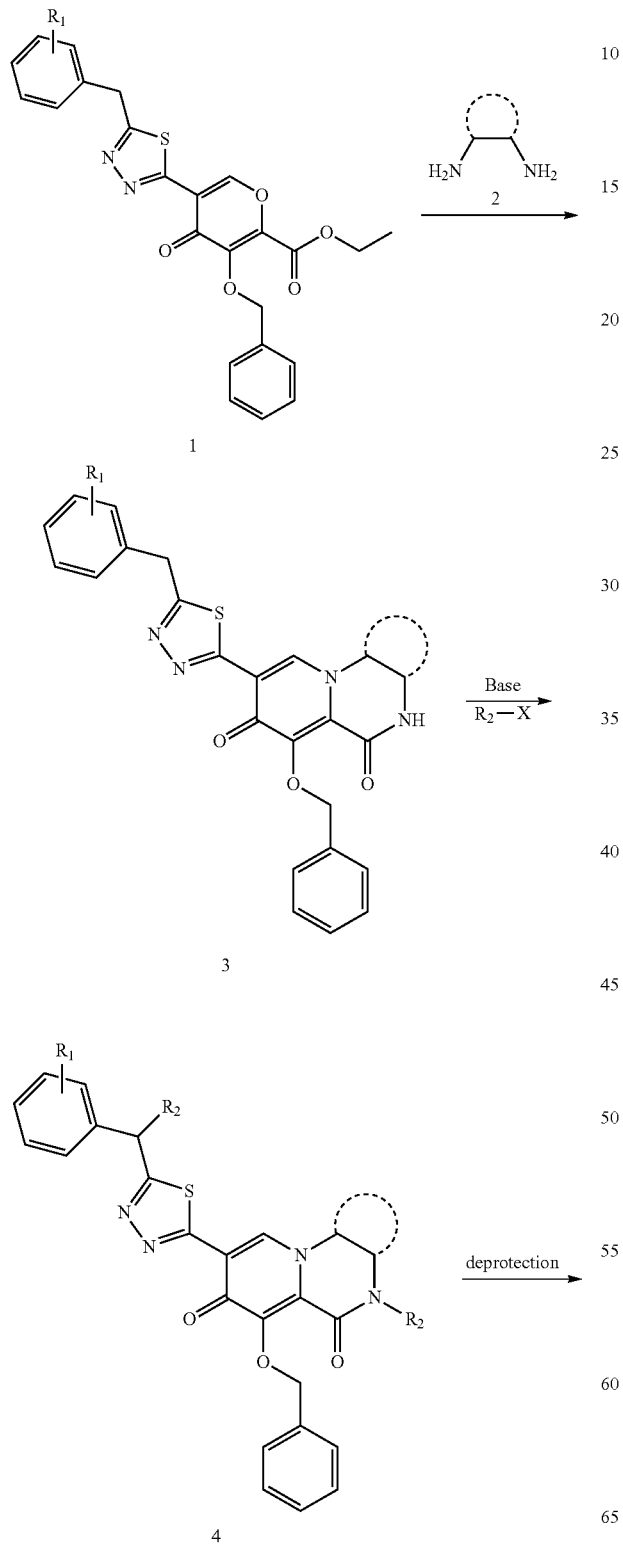

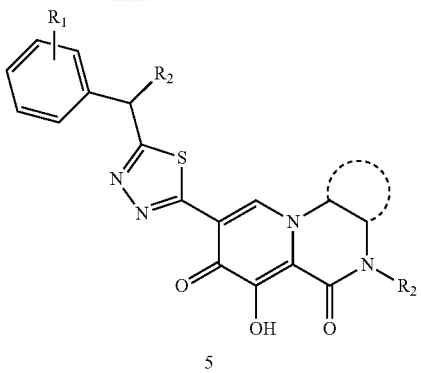

Scheme B depicts a general method for preparing compounds of the present invention wherein a cyclic diamine 2 is condensed into a pyranone 6 to provide the intermediate pyridinone which then cyclizes to form the lactam 7. This cyclization to the lactam may require a coupling reagent such as BOP. The lactam is alkylated to form 8 and then selectively halogenated with a halogenating reagent such as NBS, NIS, bromine, to form 9. Amidation under carbonylative conditions provides the amide 10, which is deprotected to provide representative HIV integrase inhibitor 11 of the present invention.

Halide 9 of Scheme B is a common intermediate. The enantiomers can be readily separated at this stage by preparative chiral SFC to provide single enantiomers that can be advanced in this and related chemistries.

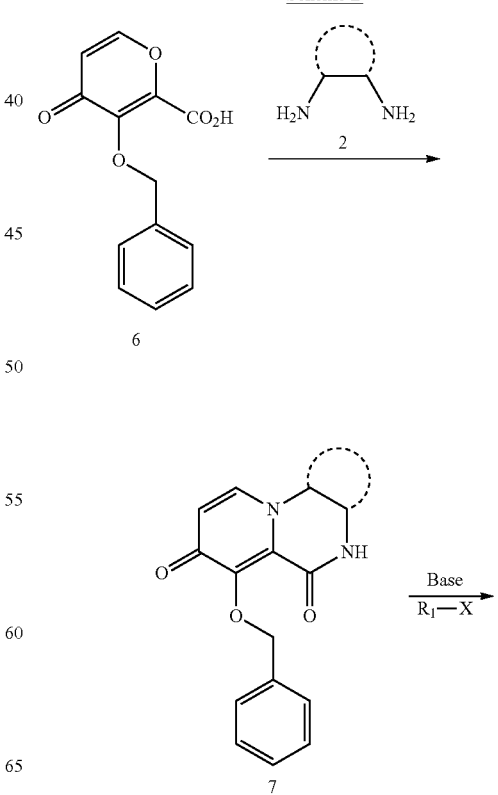

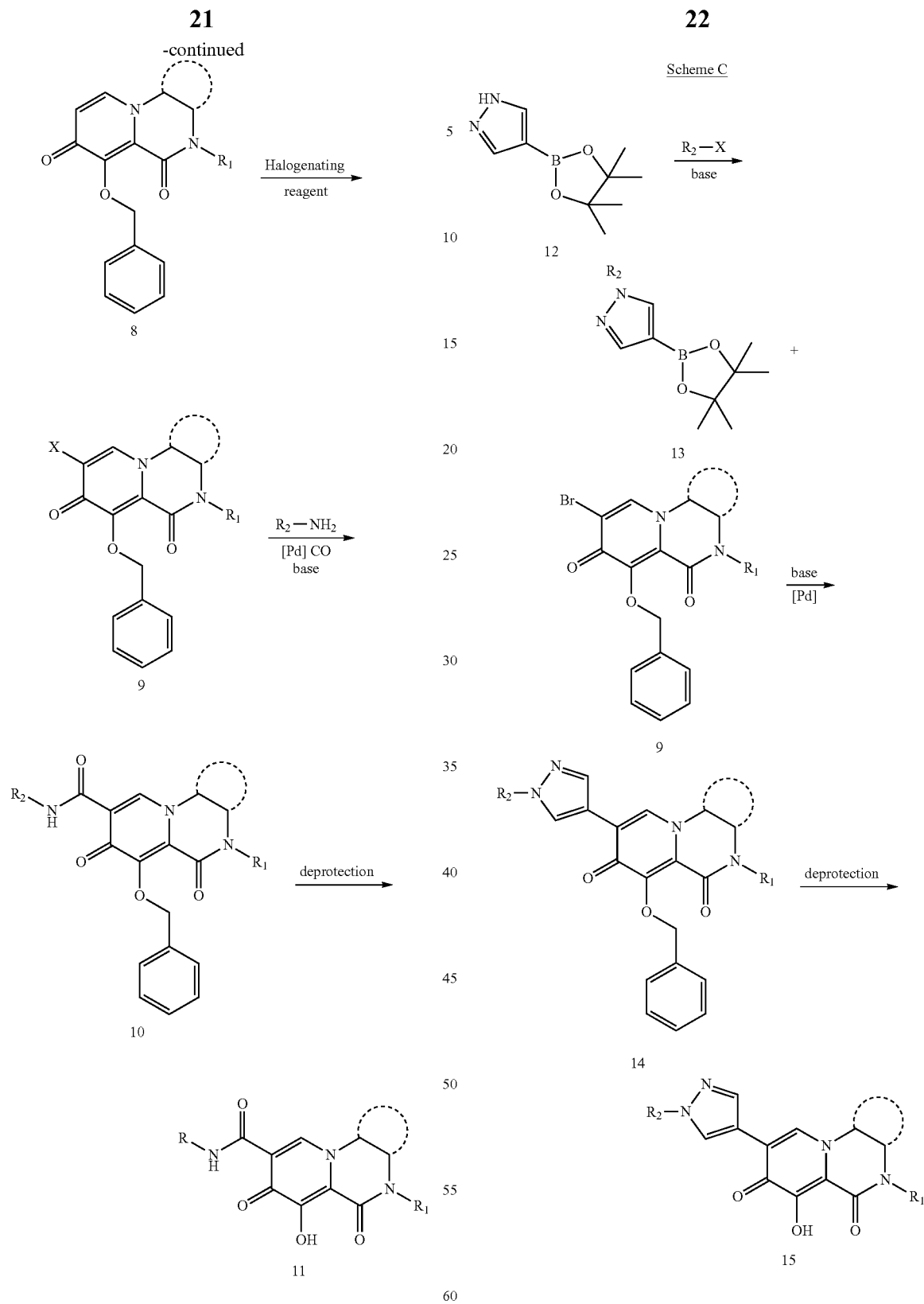

Scheme C depicts a general method for preparing compounds of the present invention wherein the pyrazole 12 is alkylated to form compound 13. Suzuki coupling with the common intermediate 9 affords the penultimate compound 14. Deprotection affords the representative HIV integrase inhibitor 11 of the present invention.

Scheme D depicts a general method for preparing compounds of the present invention wherein common intermediate 9 and TMS-acetylene react under Sonogashia coupling conditions to provide 16. Cycloaddition with azides of the form 17 provides the penultimate triazole 18. Deprotection affords the representative HIV integrase inhibitor 15 of the present invention.

Scheme D

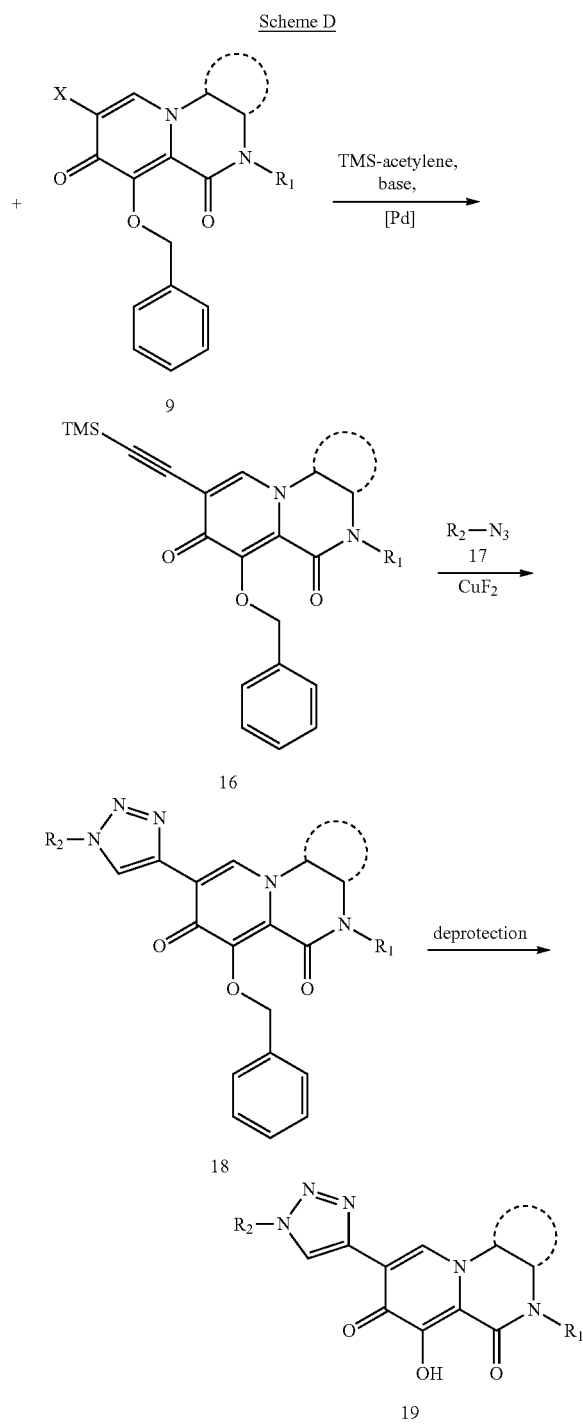

In the methods for preparing compounds of the present invention set forth in the foregoing schemes, functional groups in various moieties and substituents (in addition to those already explicitly noted in the foregoing schemes) may be sensitive or reactive under the reaction conditions employed and/or in the presence of the reagents employed. Such sensitivity/reactivity can interfere with the progress of the desired reaction to reduce the yield of the desired product, or possibly even preclude its formation. Accordingly, it may be necessary or desirable to protect sensitive or reactive groups on any of the molecules concerned. Protection can be achieved by means of conventional protecting groups, such as those described in *Protective Groups in Organic Chemistry*, ed. J. F. W. McOmie, Plenum Press, 1973 and in T. W. Greene & P. G. M. Wuts, *Protective Groups in Organic Synthesis*, John Wiley & Sons, 3$^{rd}$ edition, 1999, and 2$^{nd}$ edition, 1991. The protecting groups may be removed at a convenient subsequent stage using methods known in the art. Alternatively the interfering group can be introduced into the molecule subsequent to the reaction Step of concern.

One skilled in the art of organic synthesis will recognize that the synthesis of compounds with multiple reactive functional groups, such as —OH and NH$_2$, may require protection of certain functional groups (i.e., derivatization for the purpose of chemical compatibility with a particular reaction condition). Suitable protecting groups for the various functional groups of these compounds and methods for their installation and removal are well-known in the art of organic chemistry. A summary of many of these methods can be found in Greene & Wuts, *Protecting Groups in Organic Synthesis*, John Wiley & Sons, 3$^{rd}$ edition (1999).

One skilled in the art of organic synthesis will also recognize that one route for the synthesis of the Compounds of Formula (I) may be more desirable depending on the choice of appendage substituents. Additionally, one skilled in the relevant art will recognize that in some cases the order of reactions may differ from that presented herein to avoid functional group incompatibilities and thus adjust the synthetic route accordingly.

Compounds of formula 5, 11, 15 and 19 may be further elaborated using methods that would be well-known to those skilled in the art of organic synthesis or, for example, the methods described in the Examples below, to make the full scope of the Compounds of Formula (I).

The starting materials used and the intermediates prepared using the methods set forth in Schemes A-D may be isolated and purified if desired using conventional techniques, including but not limited to filtration, distillation, crystallization, chromatography and alike. Such materials can be characterized using conventional means, including physical constants and spectral data.

EXAMPLES

General Methods

The following examples serve only to illustrate the invention and its practice. The examples are not to be construed as limitations on the scope or spirit of the invention. In these examples, all temperatures are degrees Celsius unless otherwise noted, and "room temperature" refers to a temperature in a range of from about 20° C. to about 25° C. Mass spectra (MS) were measured by electrospray ion-mass spectroscopy (ESI). $^1$H NMR spectra were recorded on Varian or Bruker instruments at 400-500 MHz. Compounds described herein were synthesized as racemic mixtures unless otherwise stated in the experimental procedures.

Example 1

Preparation of Intermediate Compound Int-1e

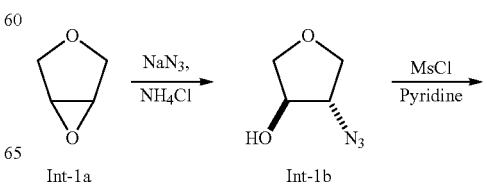

-continued

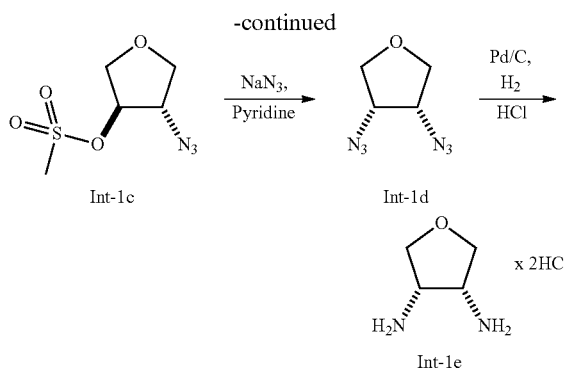

Step 1: Synthesis of Int-1b

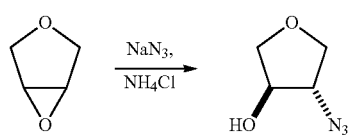 [SMILES: C1OCC2OC12 ; "NH4Cl" ; [N-]=[N+]=N[C@H]1COC[C@@H]1O]

A solution of 3,4-epoxytetrahydrofuran (170 g, 1.97 mol), ethanol (3 L), water (1.7 L), sodium azide (186 g, 2.862 mol) and ammonium chloride (153 g, 2.862 mol) was heated to reflux and allowed to stir at this temperature for 6 hours. The mixture was cooled to room temperature and most of the ethanol was removed in vacuo. Water (2.5 L) was added and the residue extracted with EtOAc (5 L×3). The organic phase was washed with brine (680 mL) and dried over sodium sulfate. The solvent was removed under reduced pressure to provide compound Int-1b, which was used without further purification.

Step 2: Synthesis of Int-1c

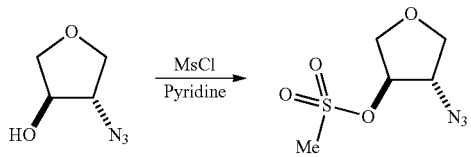 [SMILES: "MsCl" ; [N-]=[N+]=N[C@H]1COC[C@@H]1O ; "Pyridine" ; CS(=O)(=O)O[C@H]1COC[C@@H]1N=[N+]=[N-]]

A solution of mesyl chloride (49 mL, 0.631 mol) was added to a solution of trans-4-azidotetrahydrofuran-3-ol (68 g, 0.526 mol), dichloromethane (500 mL) and dry pyridine (59 mL, 0.736 mol) at 0° C. The solution was stirred over night at room temperature and then the dichloromethane was removed in vacuo. EtOAc (400 mL) was added and stirred. The resulting solid was removed by filtration, using EtOAc (100 mL) to rinse the cake. Then a 5% aqueous sodium bicarbonate solution (500 mL) was added to the filtrate. The aqueous phase was extracted with EtOAc (500 mL). The combined organic layer was washed with brine (200 mL) and dried over sodium sulfate. The solvent was removed under reduced pressure to provide compound Int-1c.

Step 3: Synthesis of Int-1d

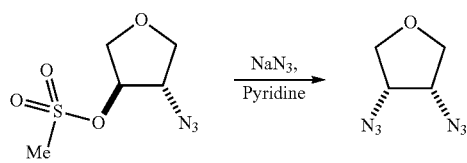 [SMILES: CS(=O)(=O)O[C@H]1COC[C@@H]1N=[N+]=[N-] ; "Pyridine" ; "NaN3," ; [N-]=[N+]=N[C@H]1COC[C@H]1N=[N+]=[N-]]

A solution of trans-4-azidotetrahydrofuran-3-yl methanesulfonate (193 g, 0.931 mol), sodium azide (121 g, 1.862 mol), DMF (2600 mL), pyridine (250 mL) and water (600 mL) was refluxed for about 15 hours. The reaction was quenched with 12 L of cold water and extracted with ether (5 L×4). The organic layer was washed with water (2 L×2) then washed with brine (1600 mL) and dried over sodium sulfate. The solvent was removed under reduced pressure. The crude product was purified using column chromatography on silica gel (PE/DCM=1:10 to DCM) to provide the compound Int-1d.

Step 4: Synthesis of Int-13

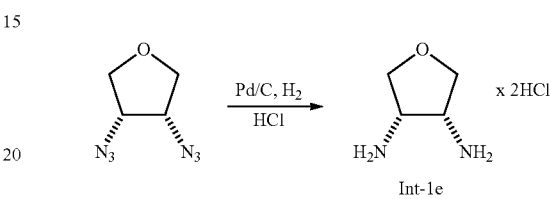

A mixture of cis-3,4-diazidotetrahydrofuran (46 g, 0.299 mol), methanol (350 mL), 10% dry palladium on carbon (10 g) and 2N hydrochloric acid (450 mL) was allowed to stir at 50 psi hydrogen over night. The reaction was filtered through celite and the filtrate concentrated under reduced pressure. The resulting residue was mixed with ethanol (250 ml) and stirred for 1 hour. The solid was collected by filtration and the cake was rinsed with ethanol (100 ml) and dried to provide the compound Int-1e. ESI-MS (M+1): 103.

Example 2

Preparation of Intermediate Compound Int-2d

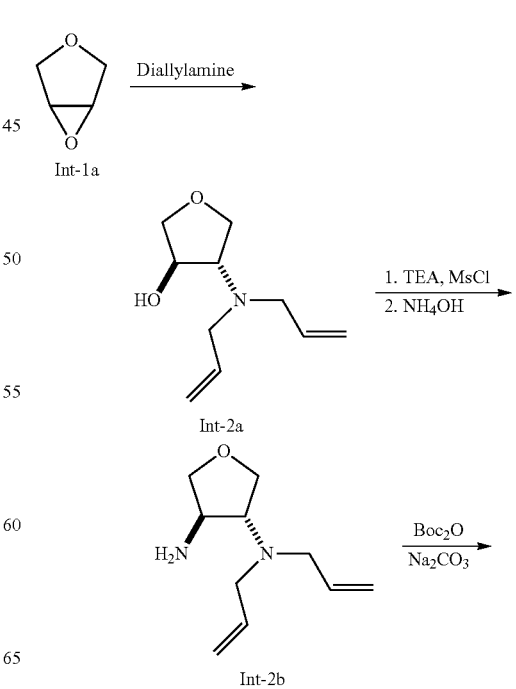

-continued

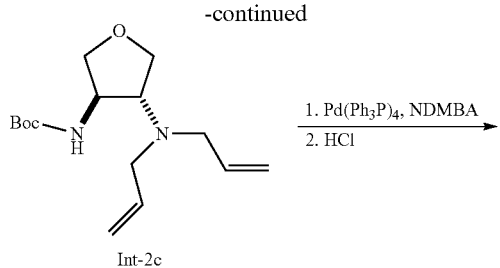

Int-2c

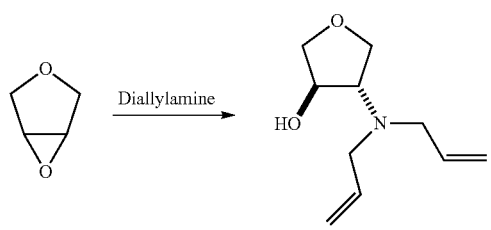

Int-2d

Step 1: Synthesis of Int-2a

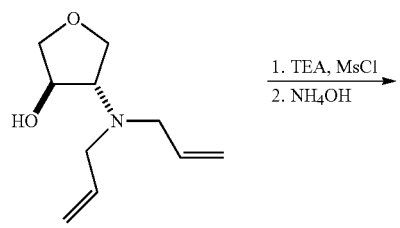

A Parr autoclave reactor was charged with 3,4-epoxytetrahydrofuran (57.4 g, 0.67 mol, diallylamine (194.3 g, 2.0 mol), and ethanol (344.4 mL). The mixture was heated to 75° C. and stirred for two days. The reaction mixture was cooled and the solvent was removed under reduced pressure to provide compound Int-2a, which was used without further purification.

Step 2: Synthesis of Int-2b

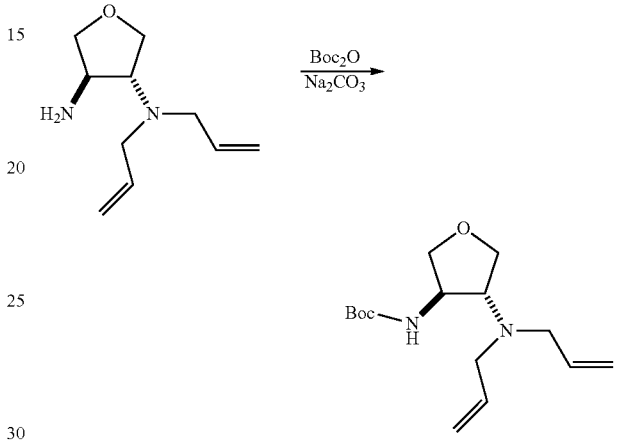

A solution of trans-4-azidotetrahydrofuran-3-ol (50.0 g, 0.273 mol) in MTBE was charged with triethylamine (44.0 g, 0.437 mol) at 5° C. Methanesulfonyl chloride (25.4 mL, 0.327 mol) was added using an addition funnel over a period of 15 min and the temperature rose to 20° C. The reaction mixture was stirred in an ice bath for 30 min. TLC analysis (9:1 EtOAc/MeOH) showed consumption of the starting material. Another portion of triethylamine (55.0 g, 0.546 mol) was added within 3 min and the reaction warmed to room temperature in 1 h. Ammonium hydroxide aqueous solution (700 mL, 29%) was added to the suspension in one portion. The resultant solution was stirred at room temperature for 16 h. The MTBE layer was separated. The water layer was extracted with MTBE (3×250 mL). The organic layers were combined and washed with brine, dried over Na₂SO₄, and concentrated under reduced pressure to provide compound Int-2b, which was used without further purification.

Step 3: Synthesis of Int-2c

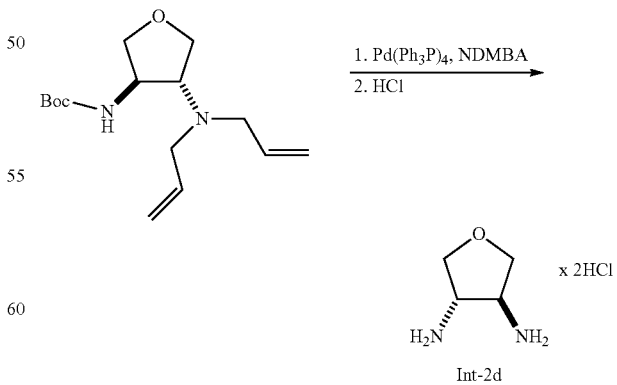

A solution of trans-N³,N³-diallyltetrahydrofuran-3,4-diamine (37.6 g, 0.20 mol) in THF (376 mL) was charged with aqueous sodium carbonate solution (32.1 g Na₂CO₃, 0.30 mol, in 300 mL water). The reaction mixture was cooled to 0-5° C.; di-tert-butyl dicarbonate (66.0 g, 0.30 mol) was added as a solid in two portions within 3 min. The reaction mixture was warmed to room temperature and stirred for 16 h. TLC analysis (5:5 heptane/MTBE) showed consumption of the starting material. The product solution was poured into 800 mL of water with stirring. The organic layer was separated. The water layer was extracted with MTBE (3×250 mL). The organic layers were combined, washed with brine, dried over Na₂SO₄, and concentrated under reduced pressure to provide compound Int-2c, which was used without further purification.

Step 4: Synthesis of Int-2d

A suspension of N,N-dimethylbarbituric acid (NDMBA; 86.9 g, 0.557 mol) and tetrakis palladium (5.5 g, 4.8 mmol) in dichloromethane (450 mL) was charged with tert-butyl (trans-4-(diallylamino)tetrahydrofuran-3-yl)carbamate (45.0 g, 0.159 mol) under $N_2$. An orange solution was generated and the solution was allowed to stir at 35-38° C. for 1.5 h when TLC analysis (5:5 heptane/EtOAc) showed consumption of the starting material. The reaction mixture was brought to room temperature and concentrated under reduced pressure. The resulting residue was dissolved in MTBE (1000 mL) and washed with saturated sodium carbonate aqueous solution (800 mL). Slow bubbling was observed. The organic layer was separated and treated with Darco G60 carbon (8.0 g). After the carbon was removed, a saturated HCl solution in IPAc (250 mL, 2.9 M) was added slowly to the brown solution. A yellow suspension was generated which was allowed to stir at room temperature for about 15 hours. The crude solid was collected by filtration and dried. It was then suspended in a 0.4 N HCl aqueous solution (prepared by mixing 100 mL concentrated HCl with 2400 mL DI water) and heated to 60° C. The insoluble was filtered. The filtrate was washed with methylene chloride (500 mL) and separated. The aqueous phase was concentrated to 150-200 mL under reduced pressure. The resulting residue was charged with MTBE (200 mL) and ethanol (50 mL). After cooling at 0° C. for 30 min, the solid was filtered, washed with MTBE, and dried in vacuum oven for one day to provide compound Int-2d. MS (APCI): m/z=103 (M+1).

Example 3

Preparation of Intermediate Compound Int-3a

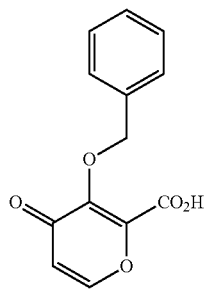

Int-3a

Compound Int-3a was made using the method described in International Publication No. WO 2010/011812.

Example 4

Preparation of Intermediate Compound Int-4a

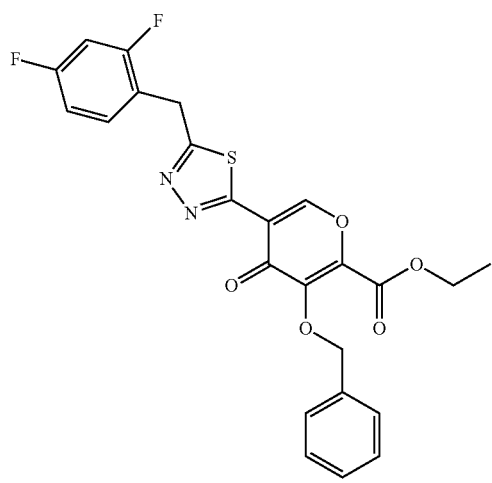

Int-4a

Compound Int-4a was made using the method described in U.S. Patent Publication No. US2012/0108564.

Example 5

Preparation of Intermediate Compound Int-5a

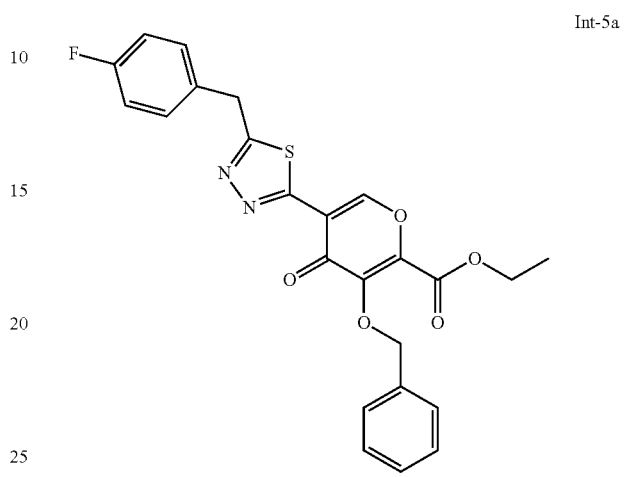

Int-5a

Compound Int-5a was made using the method described in U.S. Patent Publication No. US2012/0108564.

Example 6

Preparation of Compound 1

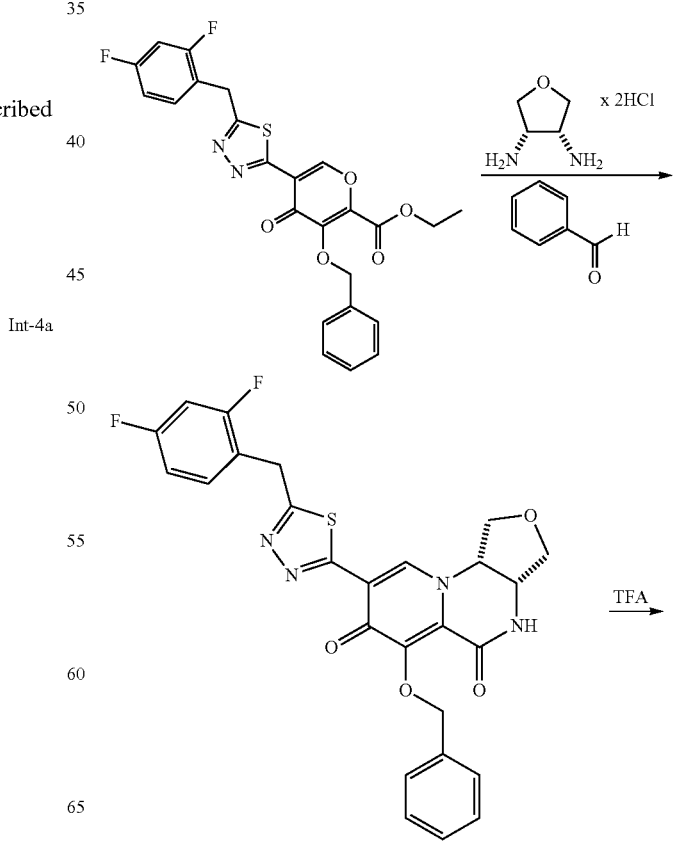

-continued

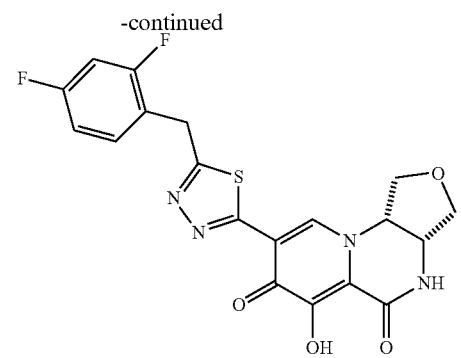

1

Step 1. cis-6-(benzyloxy)-8-(5-(2,4-difluorobenzyl)-1,3,4-thiadiazol-2-yl)-3a,4-dihydro-1H-furo[3,4-e]pyrido[1,2-a]pyrazine-5,7(3H,10aH)-dione

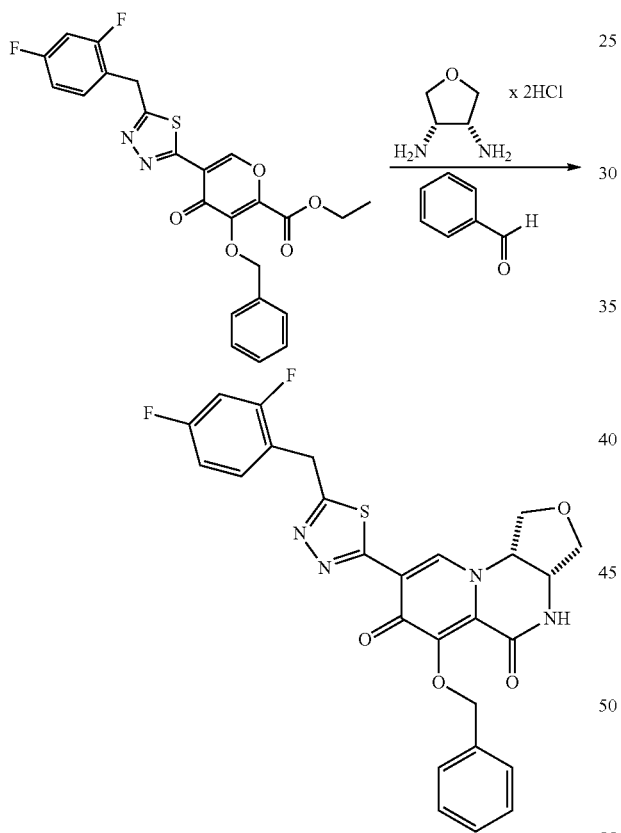

In a flame dried flask under an atmosphere of nitrogen, intermediate Int-1e (578 mg, 3.30 mmol) and benzaldehyde (0.34 mL, 3.30 mmol) was stirred in anhydrous N-methyl-imidazole (11 mL) at room temperature for about 15 hours. Intermediate Int-4a (1000 mg, 2.06 mmol) was added and the reaction was allowed to stir at room temperature for 7 more hours. Water (0.5 mL, 27.8 mmol) was added to the reaction and then stirred at room temperature for about 15 hours. The mixture was diluted with aq 1N HCl (160 mL) and extracted with EtOAc (3×100 mL). The organic layer extracts were combined, diluted with acetonitrile (10 mL), dried over Na$_2$SO$_4$, filtered, and concentrated under reduced pressure. Methanol (15 mL) was added to the residue and sonicated briefly before sitting at room temperature. The solid was collected by filtration, washed with methanol to provide the title compound. LCMS anal. calcd. for C$_{26}$H$_{20}$F$_2$N$_4$O$_4$S: 522.5. Found: 523.1 (M+1)$^+$.

Step 2. cis-8-(5-(2,4-difluorobenzyl)-1,3,4-thiadiazol-2-yl)-6-hydroxy-3a,4-dihydro-1H-furo[3,4-e]pyrido[1,2-a]pyrazine-5,7(3H,10aH)-dione (Compound 1)

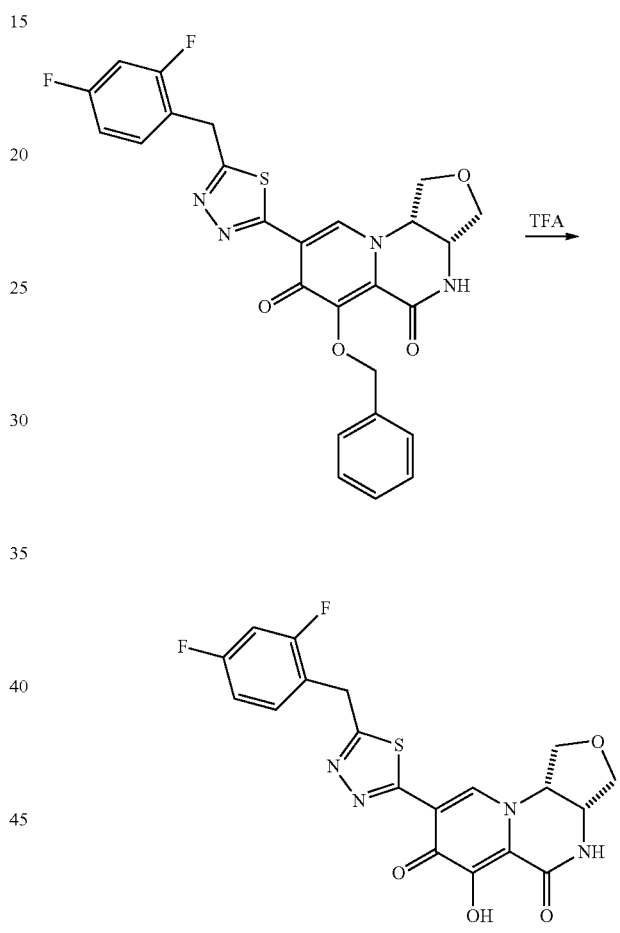

Cis-6-(benzyloxy)-8-(5-(2,4-difluorobenzyl)-1,3,4-thiadiazol-2-yl)-3a,4-dihydro-1H-furo[3,4-e]pyrido[1,2-a]pyrazine-5,7(3H,10aH)-dione (25 mg, 0.048 mmol) was dissolved in TFA (1 mL) and stirred at room temperature for 15 min. It was then cooled in an ice bath, diluted with 2:1 MeOH/water (1 mL), and purified using gradient elution on reverse phase (30×150 mm (5 um) Sunfire Prep C18; 15-65% CH$_3$CN/water w/0.1% TFA modifier over 20 min) to provide compound 1. $^1$H NMR (500 MHz, DMSO-d$_6$): δ 12.99 (s, 1H); 9.40 (s, 1H); 8.94 (s, 1H); 7.54 (m, 1H); 7.29 (m, 1H); 7.12 (m, 1H); 5.35 (m, 1H); 4.49 (s, 2H); 4.47 (m, 1H); 4.25 (t, J=8.7 Hz, 1H); 4.03 (d, J=9.9 Hz, 1H); 3.97 (dd, J=9.9, 3.4 Hz, 1H); 3.76 (t, J=8.6 Hz, 1H). LCMS anal. calcd. for C$_{19}$H$_{14}$F$_2$N$_4$O$_4$S: 432.1. Found: 433.1 (M+1)$^+$.

Example 7

Preparation of Compound 2

Step 1. trans-6-(benzyloxy)-8-(5-(2,4-difluorobenzyl)-1,3,4-thiadiazol-2-yl)-3a,4-dihydro-1H-furo[3,4-e]pyrido[1,2-a]pyrazine-5,7(3H,10aH)-dione

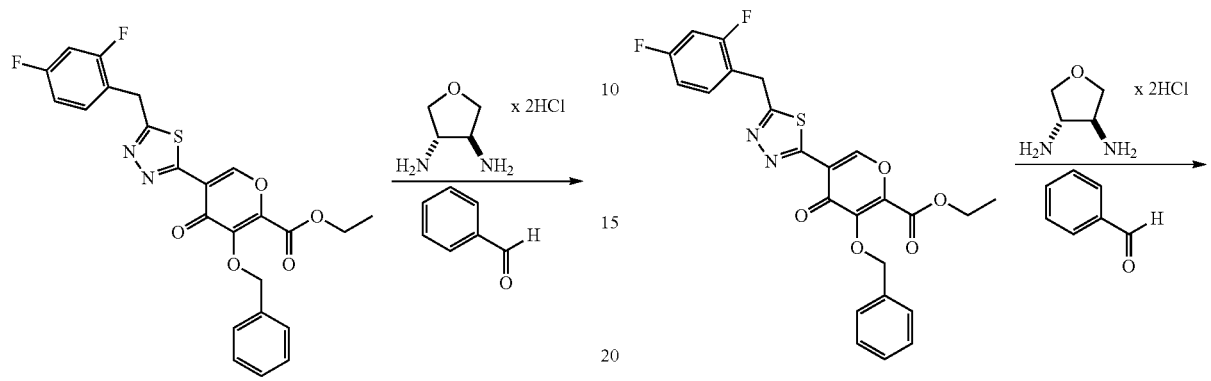

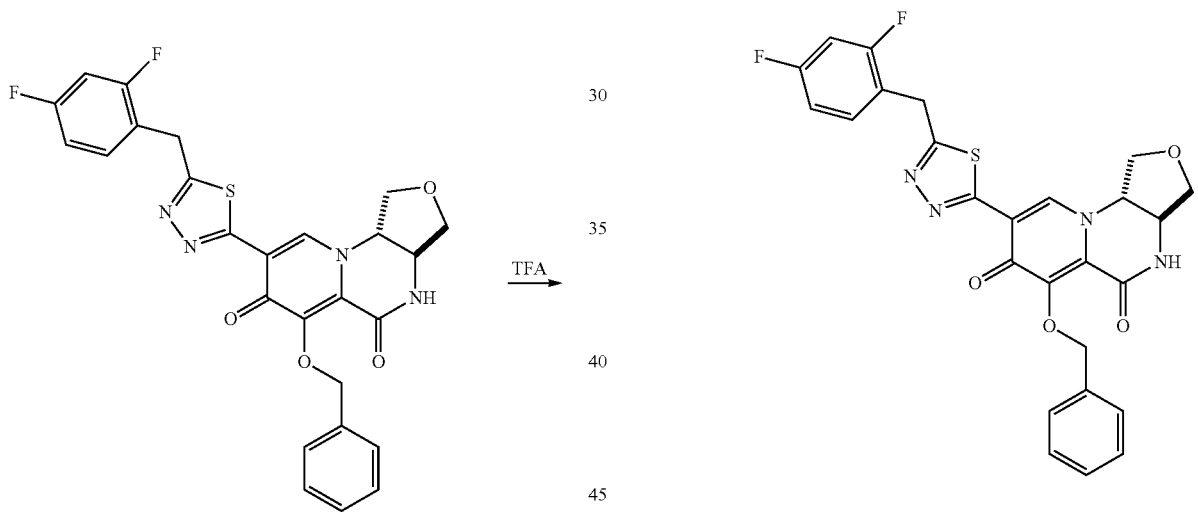

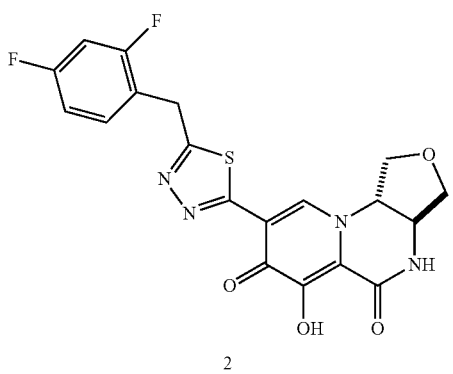

A solution of intermediate Int-2d (50 mg, 0.10 mmol) and intermediate Int-4c (20 mg, 0.11 mmol) was stirred in anhydrous N-methylimidazole (1 mL) at room temperature for about 15 hours. The reaction was then stirred for about 15 hours at 80° C. The reaction was diluted with methanol and purified using gradient elution on reverse phase (30×150 mm (5 um) Sunfire Prep C18; 20-65% $CH_3CN$/water w/0.1% TFA modifier over 20 min). The appropriate fractions were combined, the pH adjusted to pH 6 with aq sodium bicarbonate, diluted with brine, and extracted with dichloromethane (3×50 mL). The combined organic phases were dried over $Na_2SO_4$, filtered, and concentrated in vacuo. to provide the title compound. LCMS anal. calcd. for $C_{26}H_{20}F_2N_4O_4S$: 522.5. Found: 523.1 (M+1)$^+$.

Step 2. trans-8-(5-(2,4-difluorobenzyl)-1,3,4-thiadiazol-2-yl)-6-hydroxy-3a,4-dihydro-1H-furo[3,4-e]pyrido[1,2-a]pyrazine-5,7(3H,10aH)-dione (Compound 2)

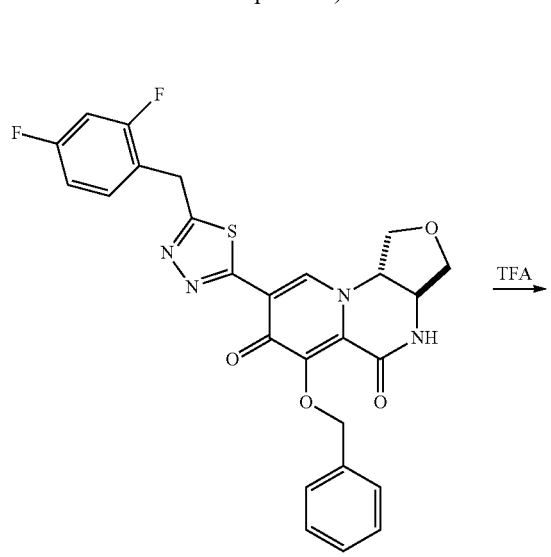

Example 8

Preparation of Compound 3

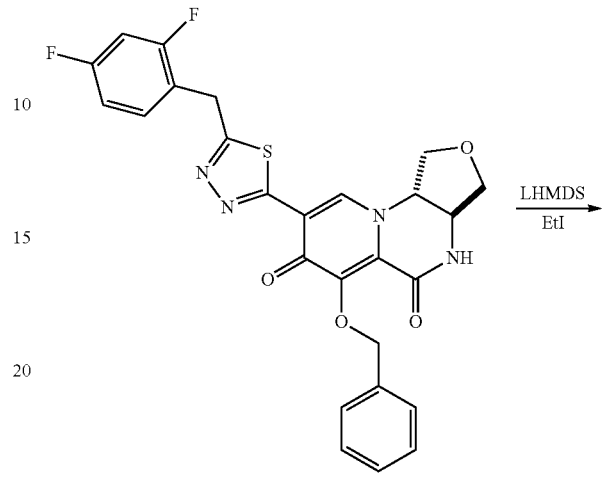

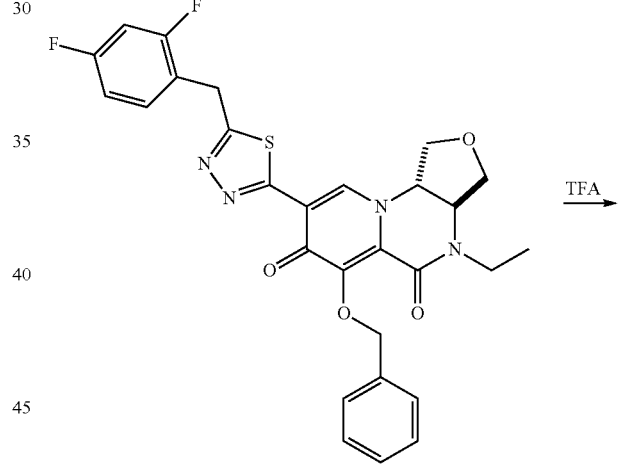

Trans-6-(benzyloxy)-8-(5-(2,4-difluorobenzyl)-1,3,4-thiadiazol-2-yl)-3a,4-dihydro-1H-furo[3,4-e]pyrido[1,2-a]pyrazine-5,7(3H,10aH)-dione (4 mg, 0.008 mmol) was dissolved in TFA (0.4 mL) and stirred at room temperature for 15 min. It was then cooled in an ice bath, diluted with 2:1 MeOH/water (1 mL), and purified using gradient elution on reverse phase (30×150 mm (5 um) Sunfire Prep C18; 15-60% CH$_3$CN/water w/0.1% TFA modifier over 15 min) to provide compound 2. $^1$H NMR (499 MHz, DMSO-d$_6$): δ 12.57 (s, 1H); 9.76 (s, 1H); 8.25 (s, 1H); 7.53 (m, 1H); 7.29 (m, 1H); 7.12 (m, 1H); 4.63 (m, 2H); 4.49 (s, 2H); 4.26 (m, 1H); 4.15-4.08 (m, 2H); 3.71 (t, J=9.1 Hz, 1H). LCMS anal. calcd. for C$_{19}$H$_{14}$F$_2$N$_4$O$_4$S: 432.1. Found: 433.1 (M+1)$^+$.

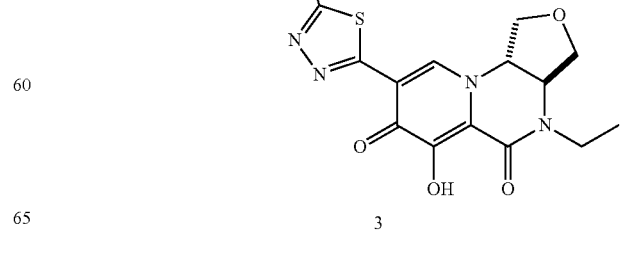

3

Step 1. trans-6-(benzyloxy)-8-(5-(2,4-difluorobenzyl)-1,3,4-thiadiazol-2-yl)-4-ethyl-3a,4-dihydro-1H-furo[3,4-e]pyrido[1,2-a]pyrazine-5,7(3H,10aH)-dione Step 2. trans-8-(5-(2,4-difluorobenzyl)-1,3,4-thiadiazol-2-yl)-4-ethyl-6-hydroxy-3a,4-dihydro-1H-furo[3,4-e]pyrido[1,2-a]pyrazine-5,7(3H,10aH)-dione (Compound 3)

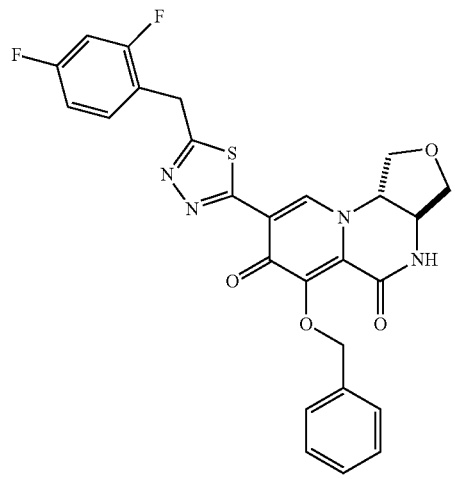

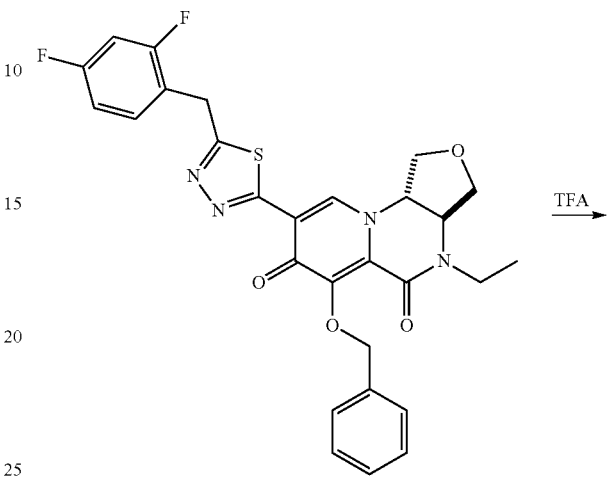

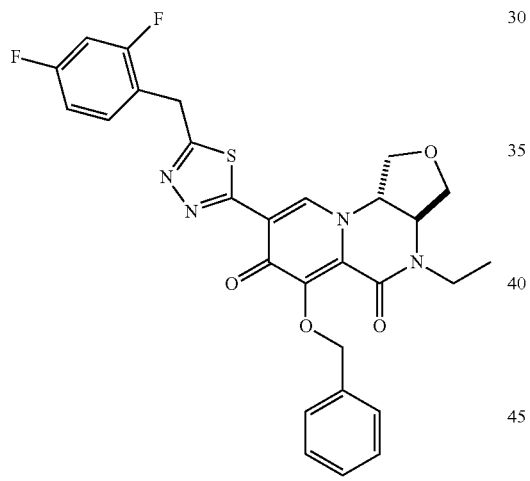

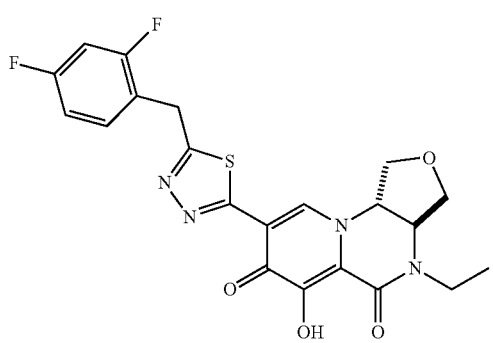

Under an atmosphere of nitrogen, trans-6-(benzyloxy)-8-(5-(2,4-difluorobenzyl)-1,3,4-thiadiazol-2-yl)-3a,4-dihydro-1H-furo[3,4-e]pyrido[1,2-a]pyrazine-5,7(3H,10aH)-dione (Example 7, step 1) (8 mg, 0.015 mmol) was dissolved in anhydrous DMF (2 mL) and cooled in an ice bath. A solution of LHMDS (18 uL, 1M in THF) was added dropwise and stirred for 15 minutes at 0° C. Iodoethane (2.3 uL, 0.028 mmol) was added and the reaction was slowly warmed to room temperature. The reaction was quenched with a few drops of aq. 1N HCl, diluted with water and extracted with dichloromethane (3×25 mL). The combined organic phases were dried over $Na_2SO_4$, filtered, and concentrated in vacuo. The compound was used without further purification. LCMS anal. calcd. for $C_{28}H_{24}F_2N_4O_4S$: 550.1. Found: 551.2 (M+1)$^+$.

Trans-6-(benzyloxy)-8-(5-(2,4-difluorobenzyl)-1,3,4-thiadiazol-2-yl)-4-ethyl-3a,4-dihydro-1H-furo[3,4-e]pyrido[1,2-a]pyrazine-5,7(3H,10aH)-dione (5 mg, 0.009 mmol) was dissolved in TFA (0.4 mL) and stirred at room temperature for 15 min. It was then cooled in an ice bath, diluted with 2:1 MeOH/water (1 mL), and purified using gradient elution on reverse phase (30×150 mm (5 um) Sunfire Prep C18; 15-60% $CH_3CN$/water w/0.1% TFA modifier over 15 min) to provide compound 3. $^1$H NMR (499 MHz, DMSO-$d_6$): δ 12.59 (s, 1H); 8.22 (s, 1H); 7.54 (m, 1H); 7.29 (m, 1H); 7.12 (m, 1H); 4.77 (m, 1H); 4.67 (t, J=7.0 Hz, 1H); 4.49-4.41 (m, 3H); 4.36 (t, J=7.0 Hz, 1H); 4.18 (t, J=8.6 Hz, 1H); 3.95 (m, 1H); 3.75-3.65 (m, 1H); 3.26-3.17 (m, 1H); 1.15 (t, J=7.1 Hz, 3H). LCMS anal. calcd. for $C_{21}H_{18}F_2N_4O_4S$: 460.1. Found: 461.1 (M+1)$^+$.

Example 9
Preparation of Compounds 4 and 5
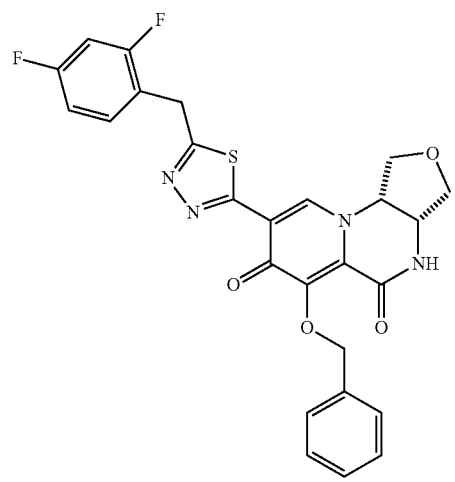
→ LHMDS / EtI
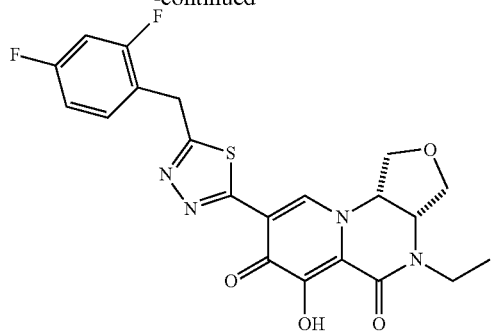
4/5
Step 1. Enantiomers A and B of cis-6-(benzyloxy)-8-(5-(2,4-difluorobenzyl)-1,3,4-thiadiazol-2-yl)-4-ethyl-3a,4-dihydro-1H-furo[3,4-e]pyrido[1,2-a]pyrazine-5,7(3H,10aH)-dione and cis-6-(benzyloxy)-8-(5-(1-(2,4-difluorophenyl)propyl)-1,3,4-thiadiazol-2-yl)-3a,4-dihydro-1H-furo[3,4-e]pyrido[1,2-a]pyrazine-5,7(3H,10aH)-dione
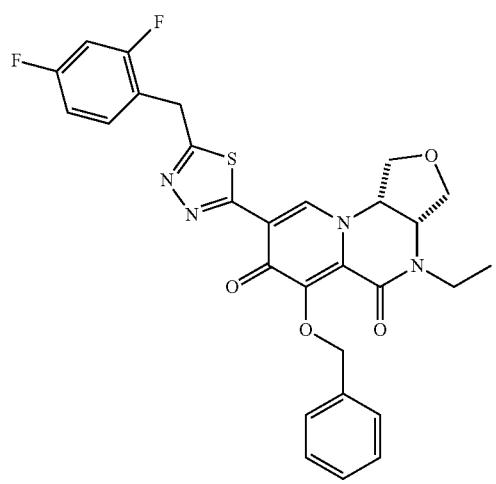
and
enantiomers separated
↓ TFA
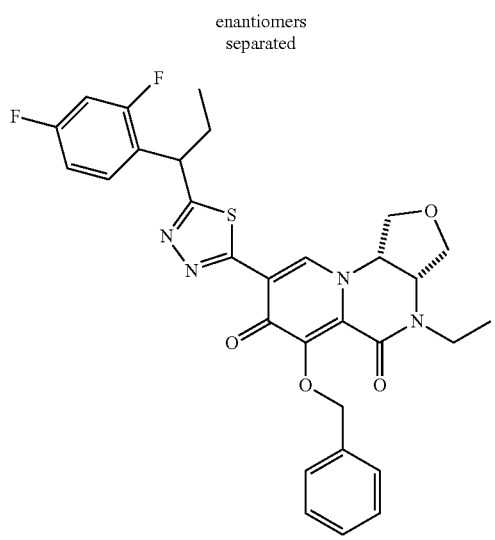
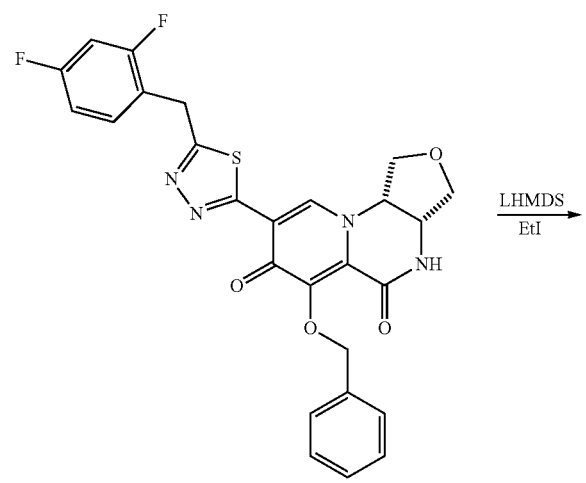
→ LHMDS / EtI
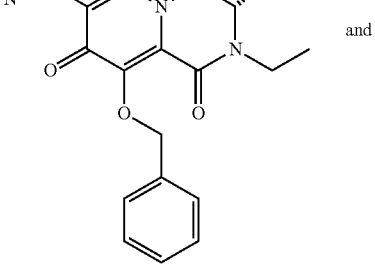
and
enantiomers separated -continued

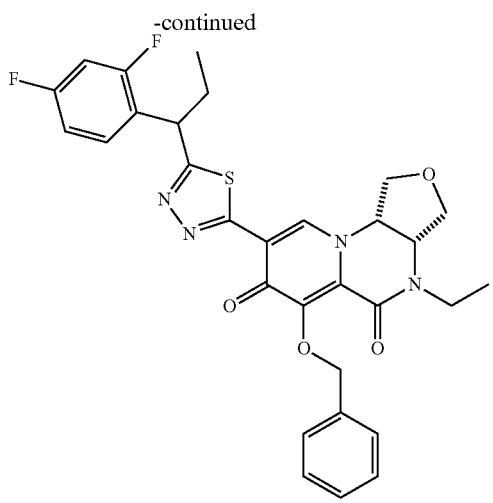

Under an atmosphere of nitrogen, cis-6-(benzyloxy)-8-(5-(2,4-difluorobenzyl)-1,3,4-thiadiazol-2-yl)-3a,4-dihydro-1H-furo[3,4-e]pyrido[1,2-a]pyrazine-5,7(3H,10aH)-dione (Example 6, step 1) (280 mg, 0.536 mmol) was dissolved in anhydrous DMF (8 mL) and cooled in a dry ice/acetone bath at −20° C. A solution of LHMDS (570 uL, 1M in THF) was added dropwise and stirred for 20 minutes at −20° C. Iodoethane (65 uL, 0.804 mmol) was added and the reaction was warmed to room temperature. After 2 hours, the reaction was quenched with aq. 1N HCl (2 mL), diluted with water, and extracted with dichloromethane (4×50 mL). The combined organic phases were dried over $Na_2SO_4$, filtered, and concentrated in vacuo. The material was purified using gradient elution on reverse phase (50×250 mm (10 um) Sunfire Prep C18; 25-75% $CH_3CN$/water w/0.1% TFA modifier over 30 min) to provide the title compound as well as cis-6-(benzyloxy)-8-(5-(1-(2,4-difluorophenyl)propyl)-1,3,4-thiadiazol-2-yl)-3a,4-dihydro-1H-furo[3,4-e]pyrido[1,2-a]pyrazine-5,7(3H,10aH)-dione. The appropriate fractions of the title compound were combined, the pH adjusted to 4 with aq sodium bicarbonate, diluted with brine, and extracted with dichloromethane (3×50 mL). The combined organic phases were dried over $Na_2SO_4$, filtered, and concentrated in vacuo. The enantiomers of the title compound were then separated using chiral preparative SFC (2×25 cm Chiralcel OJ-H, 30% MeOH with 0.1% DEA modifier/70% $CO_2$, 50 mL/min, 220 nM). The combined fractions for each enantiomer were concentrated in vacuo.

Earlier eluting enantiomer A of cis-6-(benzyloxy)-8-(5-(2,4-difluorobenzyl)-1,3,4-thiadiazol-2-yl)-4-ethyl-3a,4-dihydro-1H-furo[3,4-e]pyrido[1,2-a]pyrazine-5,7(3H,10aH)-dione. LCMS anal. calcd. for $C_{28}H_{24}F_2N_4O_4S$: 550.6. Found: 551.2 (M+1)$^+$.

Later eluting enantiomer B of cis-6-(benzyloxy)-8-(5-(2,4-difluorobenzyl)-1,3,4-thiadiazol-2-yl)-4-ethyl-3a,4-dihydro-1H-furo[3,4-e]pyrido[1,2-a]pyrazine-5,7(3H,10aH)-dione. LCMS anal. calcd. for $C_{28}H_{24}F_2N_4O_4S$: 550.6. Found: 551.2 (M+1)$^+$.

Cis-6-(benzyloxy)-8-(5-(1-(2,4-difluorophenyl)propyl)-1,3,4-thiadiazol-2-yl)-3a,4-dihydro-1H-furo[3,4-e]pyrido[1,2-a]pyrazine-5,7(3H,10aH)-dione. LCMS anal. calcd. for $C_{30}H_{28}F_2N_4O_4S$: 578.6. Found: 579.2 (M+1)$^+$.

Step 2. Enantiomers A and B of cis-8-(5-(2,4-difluorobenzyl)-1,3,4-thiadiazol-2-yl)-4-ethyl-6-hydroxy-3a,4-dihydro-1H-furo[3,4-e]pyrido[1,2-a]pyrazine-5,7(3H,10aH)-dione (Compounds 4 and 5)

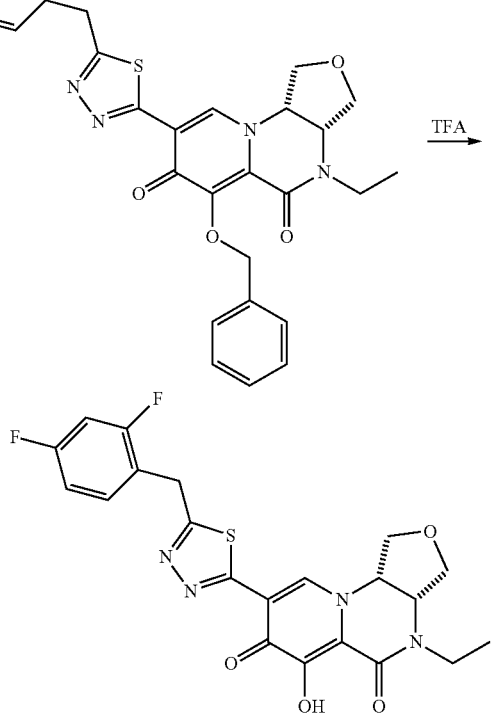

The earlier eluting enantiomer A of cis-6-(benzyloxy)-8-(5-(2,4-difluorobenzyl)-1,3,4-thiadiazol-2-yl)-4-ethyl-3a,4-dihydro-1H-furo[3,4-e]pyrido[1,2-a]pyrazine-5,7(3H, 10aH)-dione (50 mg, 0.091 mmol) was dissolved in TFA (0.5 mL) and stirred at room temperature for 15 min. It was then cooled in an ice bath, diluted with 2:1 MeOH/water (1 mL), and purified using gradient elution on reverse phase (30×150 mm (5 um) Sunfire Prep C18; 20-65% $CH_3CN$/water w/0.1% TFA modifier over 15 min) to provide enantiomer A of the title compound (compound 4). $^1$H NMR (499 MHz, DMSO-d$_6$): δ 13.15 (s, 1H); 8.89 (s, 1H); 7.54 (m, 1H); 7.29 (m, 1H); 7.12 (m, 1H); 5.32 (q, J=6.7 Hz, 1H); 4.57 (m, 1H); 4.49 (s, 2H); 4.28 (dd, J=9.3, 7.6 Hz, 1H); 4.14 (dd, J=10.3, 3.1 Hz, 1H); 4.04 (dd, J=10.3, 4.5 Hz, 1H); 3.94 (dd, J=9.3, 6.6 Hz, 1H); 3.68 (dt, J=13.9, 7.1 Hz, 1H); 3.54 (dt, J=13.9, 7.1 Hz, 1H); 1.18 (t, J=7.1 Hz, 3H). LCMS anal. calcd. for $C_{21}H_{18}F_2N_4O_4S$: 460.1. Found: 461.1 (M+1)$^+$.

The later eluting enantiomer B of cis-6-(benzyloxy)-8-(5-(2,4-difluorobenzyl)-1,3,4-thiadiazol-2-yl)-4-ethyl-3a,4-dihydro-1H-furo[3,4-e]pyrido[1,2-a]pyrazine-5,7(3H,10aH)-dione (44 mg, 0.080 mmol) was dissolved in TFA (0.5 mL) and stirred at room temperature for 15 min. It was then cooled in an ice bath, diluted with 2:1 MeOH/water (1 mL), and purified using gradient elution on reverse phase (30×150 mm (5 um) Sunfire Prep C18; 20-65% $CH_3CN$/water w/0.1% TFA modifier over 15 min) to provide enantiomer B of the title compound (compound 5). $^1$H NMR (499 MHz, DMSO-d$_6$): δ 13.15 (s, 1H); 8.89 (s, 1H); 7.54 (m, 1H); 7.29 (m, 1H); 7.12 (m, 1H); 5.32 (q, J=6.7 Hz, 1H); 4.57 (m, 1H); 4.49 (s, 2H); 4.28 (dd, J=9.3, 7.6 Hz, 1H); 4.14 (dd, J=10.3, 3.1 Hz, 1H); 4.04 (dd, J=10.3, 4.5 Hz, 1H); 3.94 (dd, J=9.3, 6.6 Hz, 1H); 3.68 (dt, J=13.9, 7.1 Hz, 1H); 3.54 (dt, J=13.9, 7.1 Hz, 1H); 1.18 (t, J=7.1 Hz, 3H). LCMS anal. calcd. for $C_{21}H_{18}F_2N_4O_4S$: 460.1. Found: 461.1 (M+1)$^+$.

The following compounds of the present invention were made using the method described in the Example above using the appropriate reactants and reagents.

| Compound | Structure | Spectroscopic Data |
|---|---|---|
| 6 [(R and S), cis-racemic] | 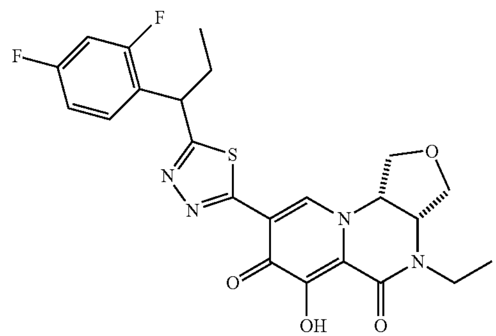 | $^1$H NMR (500 MHz, DMSO-d$_6$): δ 13.16 (s, 1 H); 8.87 (d, J = 2.5 Hz, 1 H); 7.57 (m, 1 H); 7.27 (m, 1 H); 7.13 (m, 1 H); 5.33 (m, 1 H); 4.70 (t, J = 7.6 Hz, 1 H); 4.57 (m, 1 H); 4.28 (t, J = 8.4 Hz, 1 H); 4.14 (m, 1 H); 4.04 (dd, J = 10.3, 4.4 Hz, 1 H); 3.93 (m, 1 H); 3.72-3.65 (m, 1 H); 3.67-3.50 (m 1 H); 2.37-2.29 (m, 1H); 2.17-2.10 (m, 1H); 1.18 (t, J = 7.1 Hz, 3 H); 0.91 (t, J = 7.1 Hz, 3 H). LCMS anal. calcd. for $C_{23}H_{22}F_2N_4O_4S$: 488.5; Found: 489.1 (M + 1)$^+$ |
| 7 | 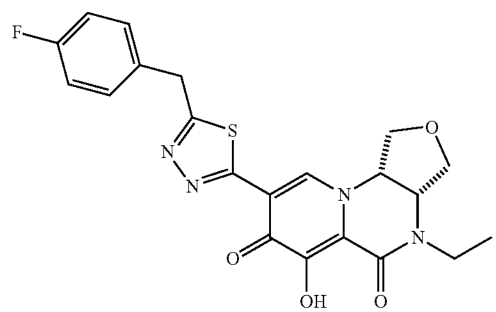 | $^1$H NMR (499 MHz, DMSO-d$_6$): δ 13.14 (s, 1 H); 8.89 (s, 1 H); 7.41 (dd, J = 8.3, 5.6 Hz, 2 H); 7.19 (t, J = 8.9 Hz, 2 H); 5.32 (m, 1 H); 4.58 (m, 1 H); 4.48 (s, 2 H); 4.28 (dd, = J = 9.3, 7.6 Hz, 1 H); 4.14 (dd, J 10.3, 3.1 Hz, 1 H); 4.04 (dd, J = 10.3, 4.5 Hz, 1 H); 3.94 (dd, J = 9.4, 6.6 Hz, 1 H); 3.67 (dt, J = 13.9, 7.1 Hz, 1 H); 3.54 (dt, J = 13.9, 7.1 Hz, 1 H); 1.18 (t, J = 7.1 Hz, 3 H). LCMS anal. calcd. for $C_{21}H_{19}FN_4O_4S$: 442.5; Found: 443.1 (M + 1)$^+$ |
| 8 | 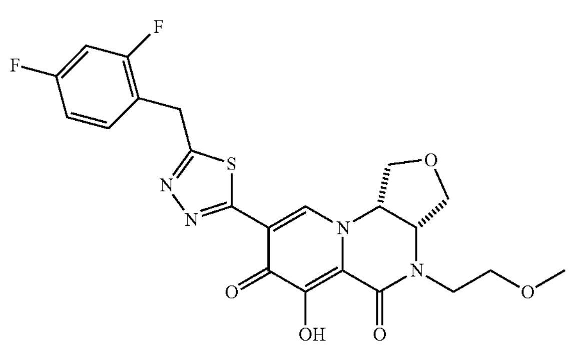 | $^1$H NMR (499 MHz, DMSO-d$_6$): δ 13.03 (s, 1 H); 8.90 (s, 1 H); 7.54 (m, 1 H); 7.29 (m, 1 H); 7.12 (m, 1 H); 5.29 (m, 1 H); 4.59 (m, 1 H); 4.50 (s, 2 H); 4.27 (dd, J = 9.4, 7.2 Hz, 1 H); 4.14 (dd, J = 10.2, 3.4 Hz, 1 H); 4.04 (dd, J = 10.2, 5.0 Hz, 1 H); 3.97 (dd, J = 9.6, 6.2 Hz 1 H); 3.93-3.87 (m, 1 H); 3.67-3.62 (m, 1H); 3.58 (t, J = 5.5 Hz, 2 H); 3.27 (s, 3 H). LCMS anal. calcd. for $C_{22}H_{20}F_2N_4O_5S$: 490.5; Found: 491.2 (M + 1)$^+$ |

| Compound | Structure | Spectroscopic Data |
|---|---|---|
| 9 | 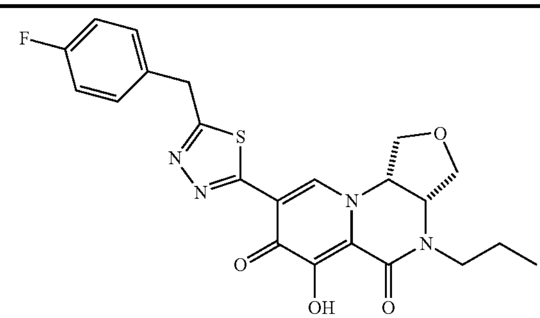 | (¹H NMR (499 MHz, DMSO-d₆): δ 13.14 (s, 1 H); 8.90 (s, 1 H); 7.41 (dd, J = 8.5, 5.6 Hz, 2 H); 7.19 (t, J = 8.8 Hz, 2 H); 5.31 (q, J = 6.6 Hz, 1 H); 4.56 (m, 1 H); 4.48 (s, 2 H); 4.28 (dd, J = 9.4, 7.4 Hz, 1 H); 4.12 (dd, J = 10.2, 3.2 Hz, 1 H); 4.04 (dd, J = 10.2, 4.7 Hz, 1 H); 3.96 (dd, J = 9.4, 6.4 Hz, 1 H); 3.67-3.60 (m, 1 H); 3.43-3.36 (m, 1H); 1.72-1.64 (m, 1 H); 1.60-1.52 (m, 1 H); 0.91 (t, J = 7.4 Hz, 3 H). LCMS anal. calcd. for $C_{22}H_{21}FN_4O_4S$: 456.5; Found: 457.1 (M + 1)⁺ |
Example 10
Preparation of Compounds 10 and 11
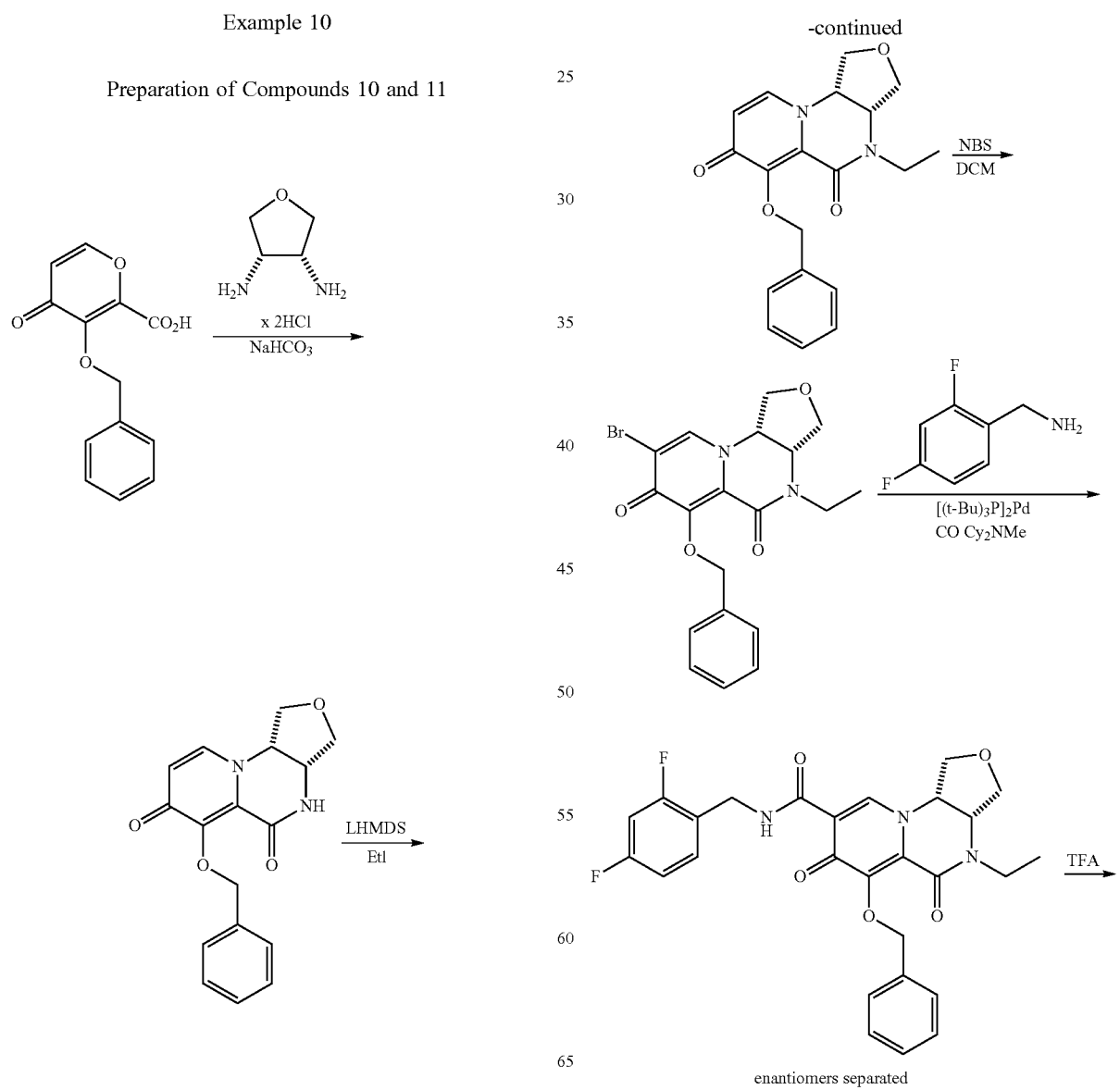

-continued

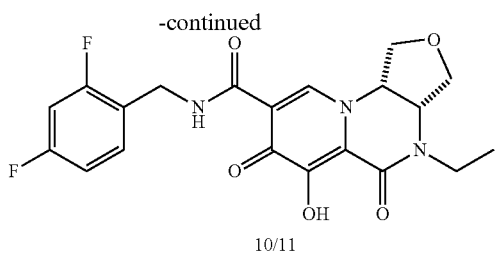

10/11

Step 1. cis-6-(benzyloxy)-3a,4-dihydro-1H-furo[3,4-e]pyrido[1,2-a]pyrazine-5,7(3H,10aH)-dione

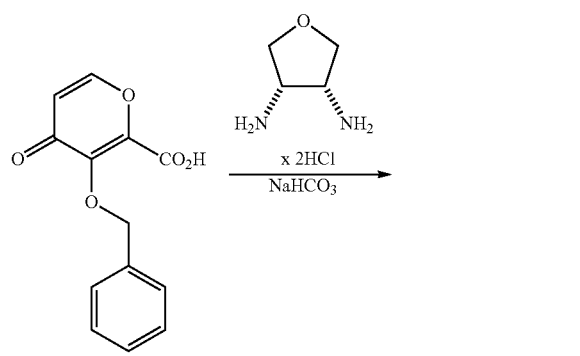

Sodium bicarbonate (8.87 g, 106 mmol) dissolved in water (150 mL). Intermediate Int-3a (14.2 g, 81 mmol) was added and stirred at room temperature for 30 minutes. Intermediate Int-1e (10 g, 40.6 mmol) was added and the solution was heated at 90° C. for about 15 hours. Additional sodium bicarbonate (690 mg, 8.2 mmol) was added and the reaction was heated at 90° C. for 48 more hours followed by sitting for about 15 hours at room temperature. The precipitated solid was collected by filtration and rinsed with water. The solid was dried in vacuo and used without further purification. LCMS anal. calcd. for $C_{17}H_{16}N_2O_4$: 312.3. Found: 313.1 (M+1)$^+$.

Step 2. cis-6-(benzyloxy)-4-ethyl-3a,4-dihydro-1H-furo[3,4-e]pyrido[1,2-a]pyrazine-5,7(3H,10aH)-dione Under an atmosphere of nitrogen, cis-6-(benzyloxy)-3a,4-dihydro-1H-furo[3,4-e]pyrido[1,2-a]pyrazine-5,7(3H,10aH)-dione (1300 mg, 4.16 mmol) was dissolved in anhydrous DMF (35 mL) and cooled in an ice bath. A solution of LHMDS (4.9 mL, 1M in THF) was added dropwise and stirred for 20 minutes at 0° C. Iodoethane (0.51 mL, 6.24 mmol) was added and the reaction was warmed to room temperature. After 2 hours the reaction was quenched with aq. 1N HCl (0.8 mL) and concentrated in vacuo. The resulting residue was diluted with brine and extracted with EtOAc (4×200 mL). The combined organic phases were dried over $Na_2SO_4$, filtered, and concentrated in vacuo. The compound was used without further purification. LCMS anal. calcd. for $C_{19}H_{20}N_2O_4$: 340.1. Found: 341.2 (M+1)$^+$.

Step 3. cis-6-(benzyloxy)-8-bromo-4-ethyl-3a,4-dihydro-1H-furo[3,4-e]pyrido[1,2-a]pyrazine-5,7(3H,10aH)-dione

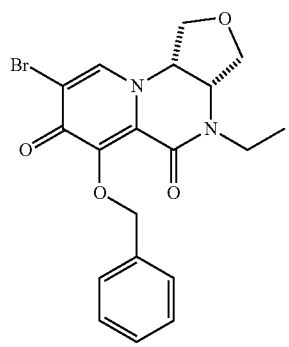

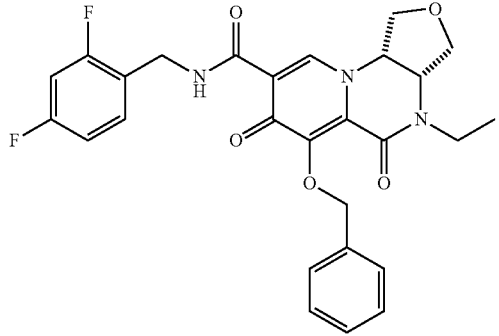

enantiomers separated

To a solution of cis-6-(benzyloxy)-4-ethyl-3a,4-dihydro-1H-furo[3,4-e]pyrido[1,2-a]pyrazine-5,7(3H,10aH)-dione (4.9 g, 14.4 mmol) in dichloromethane (200 mL) and cooled in an ice bath, was added N-bromosuccinimide (3.08 g, 17.3 mmol). The reaction was allowed to stir at room temperature for 2 hours and then quenched with aq. 1M $Na_2CO_3$. After stirring for 15 minutes, the mixture was extracted with dichloromethane (4×300 mL). The combined organic phases were dried over $Na_2SO_4$, filtered, and concentrated in vacuo. The resulting residue was purified using gradient elution on $SiO_2$ (120 g $SiO_2$, 80% to 100% EtOAc in hexanes to 5% MeOH in EtOAc) to provide the title compound. LCMS anal. calcd. for $C_{19}H_{19}BrN_2O_4$: 418.1/420.1. Found: 419.1/421.1 (M+1)$^+$.

The enantiomers can be separated using chiral preparative SFC (2×25 cm Chiralcel OD-H, 35% MeOH with 0.1% DEA modifier/65% $CO_2$, 50 mL/min, 220 nM).

Step 4. enantiomers A and B of cis-6-(benzyloxy)-N-(2,4-difluorobenzyl)-4-ethyl-5,7-dioxo-3,3a,4,5,7,10a-hexahydro-1H-furo[3,4-e]pyrido[1,2-a]pyrazine-8-carboxamide The title compounds can be prepared using the separated enantiomers of cis-6-(benzyloxy)-8-bromo-4-ethyl-3a,4-dihydro-1H-furo[3,4-e]pyrido[1,2-a]pyrazine-5,7(3H,10aH)-dione or with the racemic cis material as follows. A solution of cis-6-(benzyloxy)-8-bromo-4-ethyl-3a,4-dihydro-1H-furo[3,4-e]pyrido[1,2-a]pyrazine-5,7(3H,10aH)-dione (170 mg, 0.41 mmol) in anhydrous DMF (10 mL) was degassed with a stream of nitrogen gas. To this was added N,N-dicyclohexylmethylamine (172 uL, 0.81 mmol) and 2,4-difluorobenzylamine (200 uL, 1.68 mmol). A stream of CO gas was bubbled through the solution, bis(tri-t-butylphosphine)palladium(0) (104 mg, 0.20 mmol) was added, and a balloon filled with CO gas was attached. The reaction was heated at 90° C. for about 15 hours. The reaction was filtered, washed with dichloromethane, diluted with aq HCl, and extracted with dichloromethane (3×75 mL). The combined organic phases were dried over $Na_2SO_4$, filtered, and concentrated in vacuo. The resulting residue was purified using gradient elution on $SiO_2$ (12 g $SiO_2$, 100% EtOAc to 5% MeOH in EtOAc). The appropriate fractions were concentrated in vacuo. LCMS anal. calcd. for $C_{27}H_{25}F_2N_3O_5$: 509.2. Found: 510.1 (M+1)$^+$.

The enantiomers were separated using chiral preparative SFC (2×25 cm Chiralpak AS-H, 20% MeOH with 0.1% DEA modifier/80% $CO_2$, 50 mL/min, 220 nM). The combined fractions for each enantiomer were concentrated in vacuo.

Step 5. enantiomers A and B of cis-N-(2,4-difluorobenzyl)-4-ethyl-6-hydroxy-5,7-dioxo-3,3a,4,5,7,10a-hexahydro-1H-furo[3,4-e]pyrido[1,2-a]pyrazine-8-carboxamide (Compounds 10 and 11)

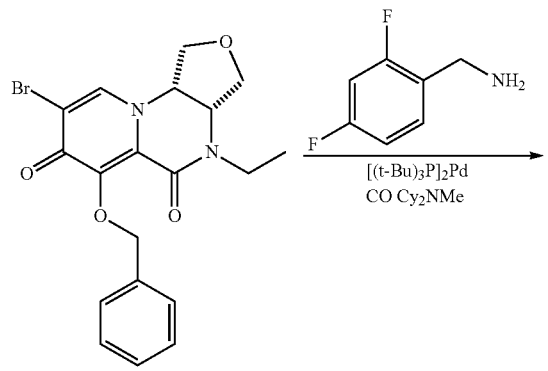 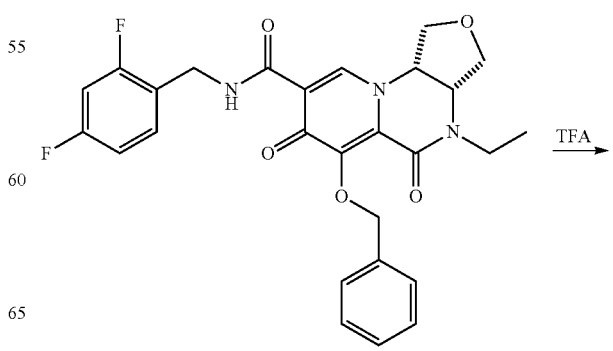

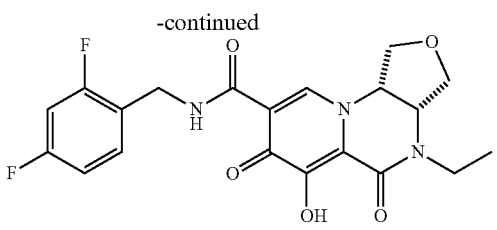

The earlier eluting enantiomer A of cis-6-(benzyloxy)-N-(2,4-difluorobenzyl)-4-ethyl-5,7-dioxo-3,3a,4,5,7,10a-hexahydro-1H-furo[3,4-e]pyrido[1,2-a]pyrazine-8-carboxamide (104 mg, 0.20 mmol) was dissolved in TFA (1.0 mL) and stirred at room temperature for 15 min. It was then cooled in an ice bath, diluted with 2:1 MeOH/water (1 mL), and purified using gradient elution on reverse phase (30×150 mm (5 um) Sunfire Prep C18; 15-60% CH$_3$CN/water w/0.1% TFA modifier over 17 min). The appropriate factions were combined, aq 1N NaOH was added to raise the pH to 12, and the aqueous was washed with dichloromethane (3×20 mL). The aqueous layer was then acidified with 1N HCl to pH3 and extracted with dichloromethane (3×40 mL). This combined organic phase was dried over Na$_2$SO$_4$, filtered, and concentrated in vacuo. to provide enantiomer A of the title compound (compound 10). $^1$H NMR (499 MHz, DMSO-d$_6$): δ 13.05 (s, 1H); 10.38 (t, J=5.9 Hz, 1H); 8.48 (s, 1H); 7.40 (m, 1H); 7.23 (m, 1H); 7.06 (m, 1H); 5.25 (q, J=6.6 Hz, 1H); 4.61-4.48 (m, 3H); 4.23 (dd, J=9.4, 7.5 Hz, 1H); 4.10 (dd, J=10.2, 3.2 Hz, 1H); 4.02 (dd, J=10.2, 4.6 Hz, 1H); 3.88 (dd, J=9.4, 6.4 Hz, 1H); 3.65 (dt, J=13.9, 7.1 Hz, 1H); 3.53 (dt, J=13.9, 7.0 Hz, 1H); 1.17 (t, J=7.1 Hz, 3H). LCMS anal. calcd. for C$_{20}$H$_{19}$F$_2$N$_3$O$_5$: 419.4. Found: 420.1 (M+1)$^+$.

The later eluting enantiomer B of cis-6-(benzyloxy)-N-(2,4-difluorobenzyl)-4-ethyl-5,7-dioxo-3,3a,4,5,7,10a-hexahydro-1H-furo[3,4-e]pyrido[1,2-a]pyrazine-8-carboxamide (77 mg, 0.15 mmol) was dissolved in TFA (1.0 mL) and stirred at room temperature for 15 min. It was then cooled in an ice bath, diluted with 2:1 MeOH/water (1 mL), and purified using gradient elution on reverse phase (30×150 mm (5 um) Sunfire Prep C18; 15-60% CH$_3$CN/water w/0.1% TFA modifier over 17 min). The appropriate factions were combined, aq 1N NaOH was added to raise the pH to 12, and the aqueous was washed with dichloromethane (3×20 mL). The aqueous layer was then acidified with 1N HCl to pH3 and extracted with dichloromethane (3×40 mL). This combined organic phase was dried over Na$_2$SO$_4$, filtered, and concentrated in vacuo to provide enantiomer B of the title compound (compound 11). $^1$H NMR (499 MHz, DMSO-d$_6$): δ 13.05 (s, 1H); 10.38 (t, J=5.9 Hz, 1H); 8.48 (s, 1H); 7.40 (m, 1H); 7.23 (m, 1H); 7.06 (m, 1H); 5.25 (q, J=6.6 Hz, 1H); 4.61-4.48 (m, 3H); 4.23 (dd, J=9.4, 7.5 Hz, 1H); 4.10 (dd, J=10.2, 3.2 Hz, 1H); 4.02 (dd, J=10.2, 4.6 Hz, 1H); 3.88 (dd, J=9.4, 6.4 Hz, 1H); 3.65 (dt, J=13.9, 7.1 Hz, 1H); 3.53 (dt, J=13.9, 7.0 Hz, 1H); 1.17 (t, J=7.1 Hz, 3H). LCMS anal. calcd. for C$_{20}$H$_{19}$F$_2$N$_3$O$_5$: 419.4. Found: 420.1 (M+1)$^+$.

The following compound of the present invention were made using the method described in the Example above using the appropriate reactants and reagents.

| Compound | Structure | Spectroscopic Data |
|---|---|---|
| 12 Cis-racemic | (structure) | $^1$H NMR (499 MHz, DMSO-d$_6$): δ 13.16 (s, 1 H); 10.40 (t, J = 5.9 Hz, 1 H); 8.54 (s, 1 H); 7.41 (m, 1 H); 7.24 (m, 1 H); 7.06 (m, 1 H); 4.92 (m, 1 H); 4.68 (m, 1 H); 4.64-4.50 (m, 3 H); 4.34 (d, J = 11.2 Hz, 1 H); 4.18 (dd, J = 11.2, 4.1 Hz, 1 H); 4.13 (t, J = 8.2 Hz, 1 H); 3.62 (t, J = 8.3 Hz, 1 H); 1.28 (d, J = 6.8 Hz, 3 H); 1.19 (d, J = 6.8 Hz, 3 H). LCMS anal. calcd. for C$_{21}$H$_{21}$F$_2$N$_3$O$_5$: 433.4; Found: 434.1 (M + 1)$^+$ |

Example 11

Preparation of Compound 13

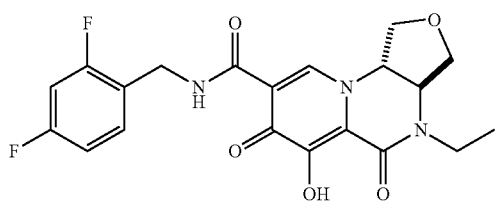

Compound 13 was made using the method described in Example 10 and replacing step 1 with steps 1a and 1b immediately described below. $^1$H NMR (500 MHz, DMSO-d$_6$): δ 12.45 (s, 1H); 10.34 (t, J=5.8 Hz, 1H); 7.86 (s, 1H); 7.39 (m, 1H); 7.23 (m, 1H); 7.06 (m, 1H); 4.70 (m, 1H); 4.59 (t, J=7.4 Hz, 1H); 4.53 (d, J=5.8 Hz, 2H); 4.43-4.36 (m, 1H); 4.34 (t, J=7.3 Hz, 1H); 4.10 (dd, J=9.8, 7.8 Hz, 1H); 3.97-3.91 (m, 1H); 3.70-3.63 (m, 1H); 3.24-3.16 (m, 1H); 1.14 (t, J=7.1 Hz, 3H). LCMS anal. calcd. for C$_{20}$H$_{19}$F$_2$N$_3$O$_5$: 419.4. Found: 420.1 (M+1)$^+$.

Step 1a. 1-(trans-4-aminotetrahydrofuran-3-yl)-3-(benzyloxy)-4-oxo-1,4-dihydropyridine-2-carboxylic acid

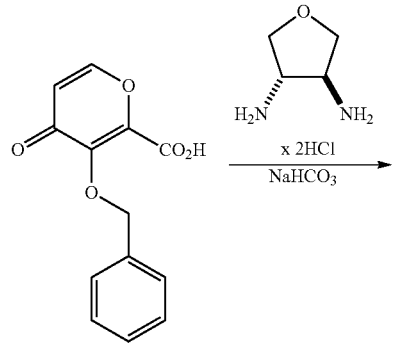

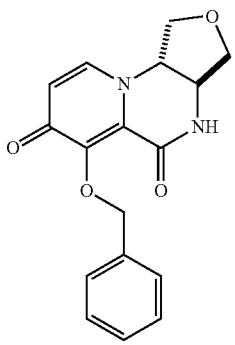

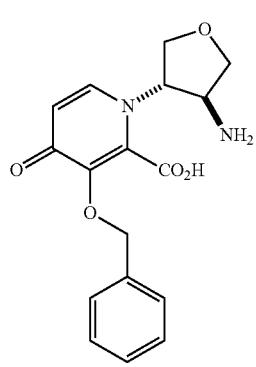

To a solution of sodium bicarbonate (819 mg, 9.75 mmol) and Intermediate Int-3a (1138 mg, 6.50 mmol) in water (5 mL) was added Intermediate Int-2d (445 mg, 1.81 mmol) and the reaction was heated at 80° C. for about 15 hours. The reaction was cooled and the precipitated solid was collected by filtration, rinsed with water, and dried in vacuo. LCMS anal. calcd. for $C_{17}H_{18}N_2O_5$: 330.3. Found: 331.1 (M+1)⁺.

Step 1b. trans-6-(benzyloxy)-3a,4-dihydro-1H-furo[3,4-e]pyrido[1,2-a]pyrazine-5,7(3H,10aH)-dione

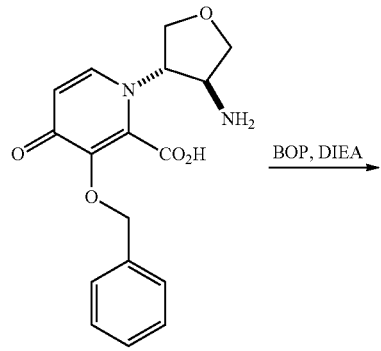

To a mixture of 1-(trans-4-aminotetrahydrofuran-3-yl)-3-(benzyloxy)-4-oxo-1,4-dihydropyridine-2-carboxylic acid (400 mg, 1.21 mmol) and DIEA (0.42 mL, 2.42 mmol) in anhydrous DMF (15 mL) was added BOP (750 mg, 1.70 mmol) and the reaction was allowed to stir at room temperature for about 15 hours. More DIEA (0.40 mL, 2.29 mmol) and BOP (700 mg, 1.59 mmol) were added and the reaction was allowed to stir at 60° C. for about 15 hours. More DIEA (0.20 mL, 1.15 mmol) and BOP (500 mg, 1.13 mmol) were added and the reaction was allowed to stir at 60° C. through the day before sitting at room temperature for about 15 hours. The reaction was acidified with aq 1N HCl, diluted with brine, and extracted with a 1:1 nBuOH/EtOAc mixture (3×100 mL). The combined organic phase was dried over $Na_2SO_4$, filtered, and concentrated in vacuo. The resulting residue was purified using gradient elution on reverse phase (50×250 mm (10 um) Sunfire Prep C18; 10-60% $CH_3CN$/water w/0.1% TFA modifier over 30 min) to provide the title compound. LCMS anal. calcd. for $C_{17}H_{16}N_2O_4$: 312.3. Found: 313.1 (M+1)⁺.

Example 12

Preparation of Compound 14

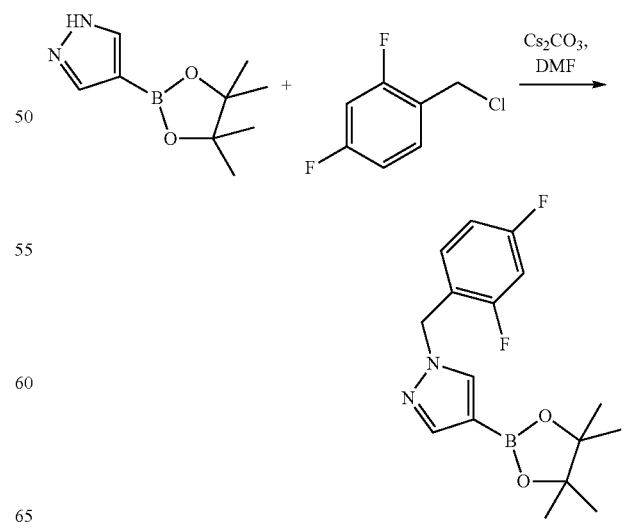

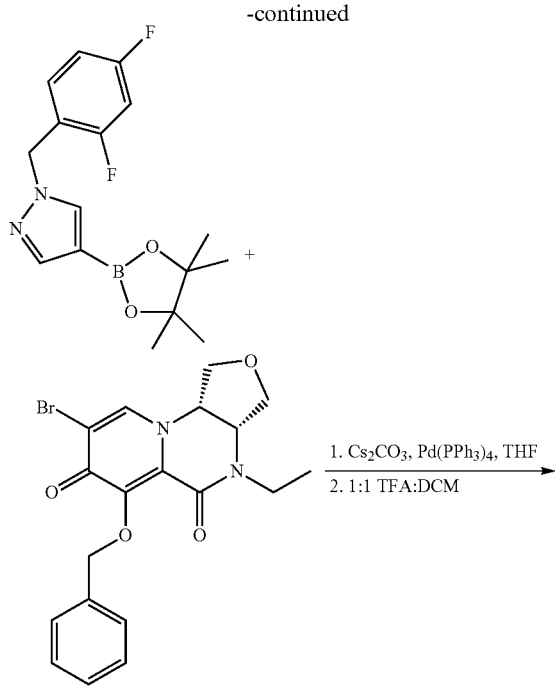

Example 10, step 3 chloride (0.943 g, 5.80 mmol), and cesium carbonate (2.52 g, 7.73 mmol) in DMF (12 mL) was allowed to stir at room temperature for 16 hours. The crude reaction mixture was filtered through a glass frit and purified using reverse phase preparatory HPLC to provide the title compound. $^1$H NMR (400 MHz, CDCl$_3$): δ 7.85 (s, 1H), 7.72 (s, 1H), 7.24-7.16 (m, 1H), 6.88-6.81 (m, 2H), 5.36 (s, 2H), 1.31 (s, 12H). LCMS anal. calcd. for $C_{16}H_{19}BF_2N_2O_2$: 320.2. Found: 321.4 (M+1)$^+$.

Step 2: cis-8-(1-(2,4-difluorobenzyl)-1H-pyrazol-4-yl)-4-ethyl-6-hydroxy-3a,4-dihydro-1H-furo[3,4-e]pyrido[1,2-a]pyrazine-5,7(3H,10aH)-dione (Compound 14)

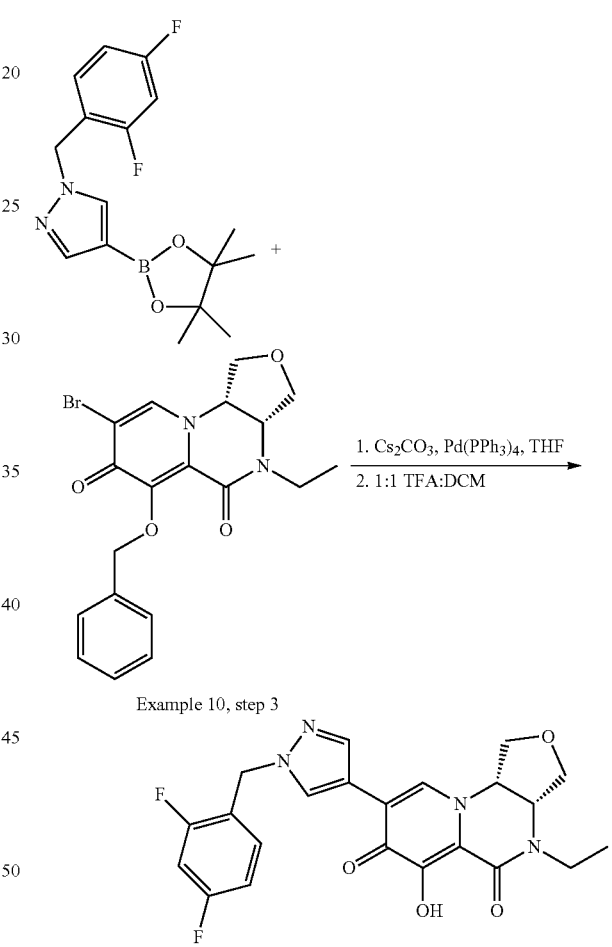

Example 10, step 3

Step 1. 1-(2,4-difluorobenzyl)-4-(4,4,5,5-tetramethyl-1,3,2-dioxaborolan-2-yl)-1H-pyrazole

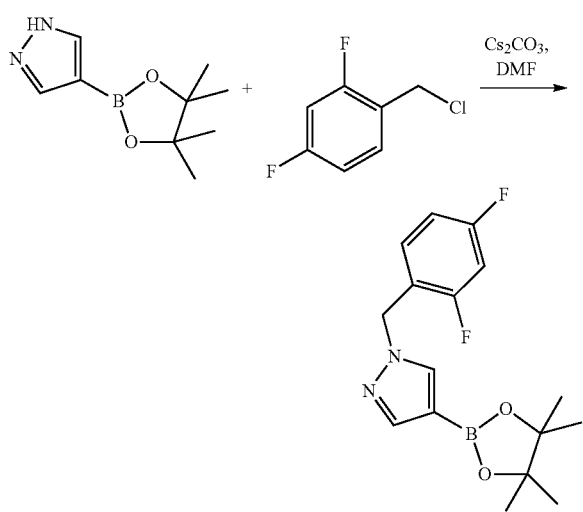

A mixture of 4-(4,4,5,5-tetramethyl-1,3,2-dioxaborolan-2-yl)-1H-pyrazole (0.750 g, 3.87 mmol), 2,4-difluorobenzyl A mixture of cis-6-(benzyloxy)-8-bromo-4-ethyl-3a,4-dihydro-1H-furo[3,4-e]pyrido[1,2-a]pyrazine-5,7(3H,10aH)-dione (see example 10, step 3) (15 mg, 0.036 mmol), 1-(2,4-difluorobenzyl)-4-(4,4,5,5-tetramethyl-1,3,2-dioxaborolan-2-yl)-1H-pyrazole (23 mg, 0.072 mmol), and cesium carbonate (23 mg, 0.072 mmol) in THF (0.5 mL) with 2 drops of water was degassed and placed under an atmosphere of nitrogen gas. Tetrakis(triphenylphosphine)palladium(0) (4.1 mg, 0.0036 mmol) was added, and the mixture was heated at 110° C. for 19 hours. The resultant reaction mixture was cooled to room temperature and diluted with ethyl acetate. The solution was washed successively with water, and brine, then dried over anhydrous sodium sulfate, filtered, and concentrated in vacuo. The crude residue was redissolved in 1:1 trifluoroacetic acid: dichloromethane (1 mL), and heated to 40° C. for 1.5 hours. The resultant reaction mixture was cooled to room temperature, concentrated in vacuo, and purified using reverse phase preparatory HPLC to provide compound 14. $^1$H NMR (400 MHz, CDCl$_3$): δ 8.43 (s, 1H), 7.83 (s, 1H), 7.67 (s, 1H), 7.26-7.13 (m, 1H), 6.87-6.82 (m, 2H), 5.31 (s, 2H), 4.92-4.90 (m, 1H), 4.41-4.32 (m, 2H), 4.19-4.08 (m, 2H), 3.99-3.95 (m, 1H), 3.58 (q, J=7.1 Hz, 2H), 1.28 (t, J=7.1 Hz, 3H). LCMS anal. calcd. for C$_{22}$H$_{20}$F$_2$N$_4$O$_4$: 442.1. Found: 443.3 (M+1)$^+$.

Example 13

Preparation of Compound 15

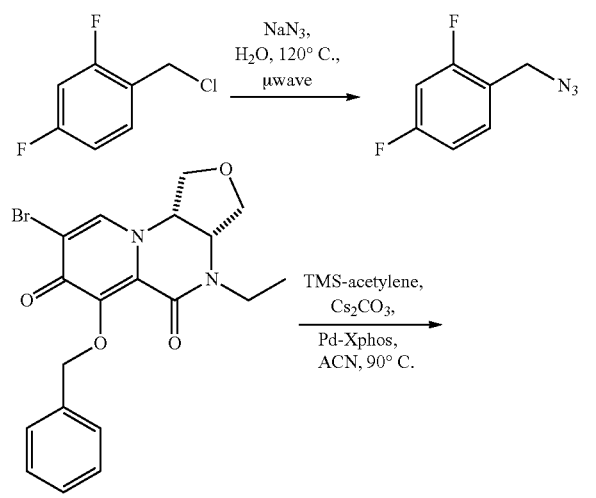

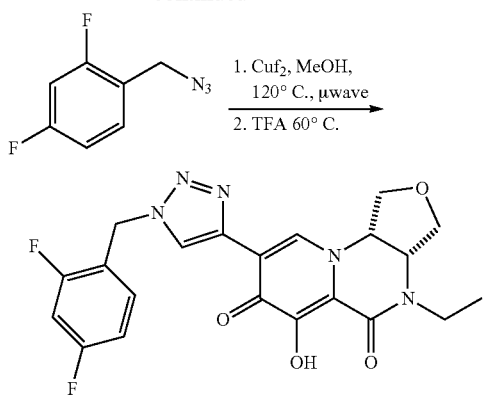

Step 1: 1-(azidomethyl)-2,4-difluorobenzene

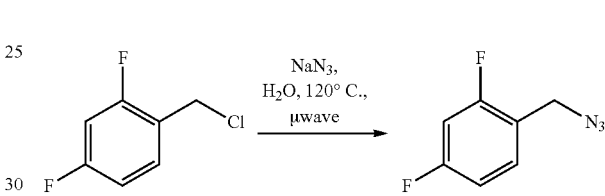

A mixture of 2,4-difluorobenzyl chloride (2.00 g, 12.3 mmol) and sodium azide (0.880 g, 13.5 mmol) in water (3 mL) was irradiated in a microwave reactor at 120° C. for 30 minutes. The resultant reaction mixture was cooled to room temperature and extracted with dichloromethane. The organic solution was washed with brine, dried over anhydrous sodium sulfate, filtered, and concentrated in vacuo to provide 1-(azidomethyl)-2,4-difluorobenzene that was used without further purification. $^1$H NMR (400 MHz, CDCl$_3$): δ 7.36-7.27 (m, 1H), 6.92-6.82 (m, 2H), 4.36 (s, 2H).

Step 2: Enantiomer A of cis-6-(benzyloxy)-4-ethyl-8-((trimethylsilyl)ethynyl)-3a,4-dihydro-1H-furo[3,4-e]pyrido[1,2-a]pyrazine-5,7(3H,10aH)-dione

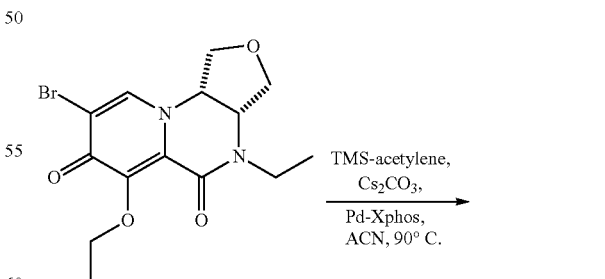

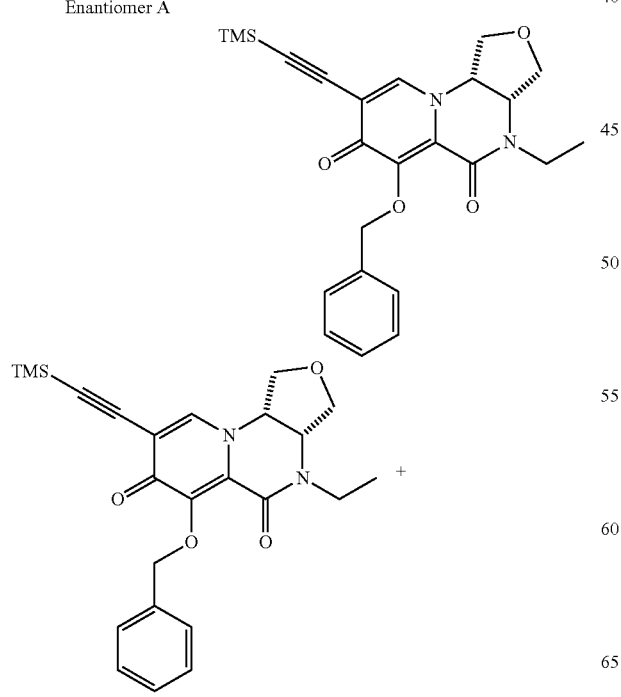

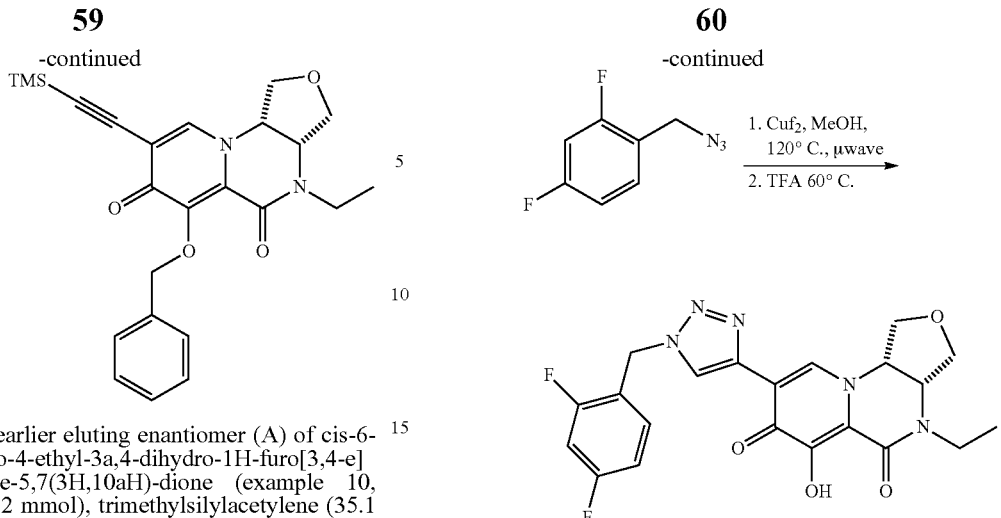

A mixture of the earlier eluting enantiomer (A) of cis-6-(benzyloxy)-8-bromo-4-ethyl-3a,4-dihydro-1H-furo[3,4-e]pyrido[1,2-a]pyrazine-5,7(3H,10aH)-dione (example 10, step 3) (30 mg, 0.072 mmol), trimethylsilylacetylene (35.1 mg, 0.358 mmol), cesium carbonate (46.6 mg, 0.143 mmol) in acetonitrile (1 mL) was degassed and placed under an atmosphere of nitrogen gas. (2-Dicyclohexylphosphino-2',4',6'-triisopropyl-1,1'-biphenyl)[2-(2-aminoethyl)phenyl]palladium(II) chloride (13 mg, 0.018 mmol) was added, and the mixture was heated at 90° C. for 1.5 hours. The resultant reaction mixture was cooled to room temperature and purified directly using flash chromatography on silica gel (0-100% ethyl acetate/hexanes) to provide the title compound. $^1$H NMR (400 MHz, CDCl$_3$): δ 7.66 (d, J=7.3 Hz, 2H), 7.52 (s, 1H), 7.35-7.26 (m, 3H), 5.42 (d, J=9.9 Hz, 1H), 5.22 (d, J=9.9 Hz, 1H), 4.59-4.55 (m, 1H), 4.31-4.19 (m, 2H), 4.13-4.09 (m, 2H), 3.80-3.76 (m, 1H), 3.65-3.60 (m, 2H), 1.25 (d, J=7.5 Hz, 3H), 0.26 (s, 9H). LCMS anal. calcd. for C$_{24}$H$_{28}$N$_2$O$_4$Si: 436.2. Found: 437.4 (M+1)$^+$.

Step 3: Enantiomer A of cis-8-(1-(2,4-Difluorobenzyl)-1H-1,2,3-triazol-4-yl)-4-ethyl-6-hydroxy-3a,4-dihydro-1H-furo[3,4-e]pyrido[1,2-a]pyrazine-5,7(3H,10aH)-dione (Compound 15)

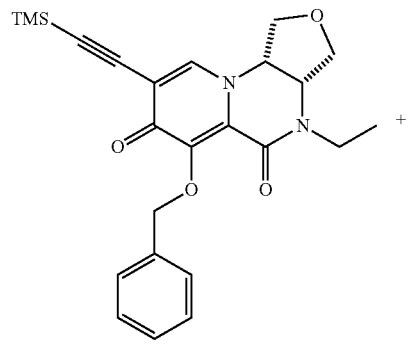

A mixture of 1-(azidomethyl)-2,4-difluorobenzene (11 mg, 0.064 mmol) and enantiomer A of cis-6-(benzyloxy)-4-ethyl-8-((trimethylsilyl)ethynyl)-3a,4-dihydro-1H-furo[3,4-e]pyrido[1,2-a]pyrazine-5,7(3H,10aH)-dione (14 mg, 0.032 mmol) in methanol (0.5 mL) was degassed and placed under an atmosphere of nitrogen gas. Copper(II) fluoride (6.5 mg, 0.064 mmol) was added, and the mixture was irradiated in a microwave reactor at 120° C. for 20 minutes. The resultant reaction mixture was cooled to room temperature, filtered via a syringe filter, and concentrated in vacuo. Trifluoroacetic acid (0.5 mL) was added to the crude residue, and the mixture was heated to 80° C. for 3 hours. The resultant reaction mixture was cooled to room temperature, concentrated in vacuo, and purified using reverse phase preparatory HPLC to provide enantiomer A (compound 15) as a beige solid. $^1$H NMR (400 MHz, CDCl$_3$): δ 8.70 (s, 1H), 8.48 (s, 1H), 7.32-7.26 (m, 1H), 6.91-6.87 (m, 2H), 5.58 (s, 2H), 5.00-4.95 (m, 1H), 4.47-4.38 (m, 2H), 4.24-4.04 (m, 3H), 3.81-3.72 (m, 1H), 3.64-3.56 (m, 1H), 1.32 (t, J=7.1 Hz, 3H). LCMS anal. calcd. for C$_{21}$H$_{19}$F$_2$N$_5$O$_4$: 443.1. Found: 444.3 (M+1)$^+$.

The following compound of the present invention was made using the method described in the Example above using the appropriate reactants and reagents.

| Compound | Structure | Spectroscopic Data |
|---|---|---|
| 16 (Enantiomer B) | ![structure] | LCMS anal. calcd. for C$_{21}$H$_{19}$F$_2$N$_5$O$_4$: 443.1; Found: 444.3 (M + 1)$^+$ |

Example 14

Assay for Inhibition of HIV Replication

This assay is a kinetic assay that employs a reporter cell line (MT4-gag-GFP) to quantify the number of new cells infected in each round of replication.

MT4-GFP cells (250,000 cells/ml) were bulk-infected with HIV-1 (NL4-3 strain) at low multiplicity of infection (MOI) in RPMI+10% FBS for 24 hours. Cells were then washed once in RPMI+10% FBS and resuspended in RPMI+0% or 10% or 100% normal human serum (NHS). Test compounds were serial-diluted in DMSO on ECHO. The infected MT4-GFP cells were added to a 384-well poly-D-lysine coated black plate with clear bottom in which the diluted test compounds were placed. The cells were seeded at 8,000 cells per well and the final DMSO concentration was 0.4%. The infected cells (Green GFP cells) were quantified at both 24 and 48 hours post incubation using Acumen eX3. Viral reproductive ratio ($R_0$) was determined using the number of infected cells at 48 hours divided by the number of infected cells at 24 hours. Percent viral growth inhibition was calculated by $[1-(R-R_{tripledrug})/(R_{DMSO}-R_{tripledrug})]*100$. Compound potency IP or $IC_{50}$ was determined by a 4-parameter dose response curve analysis.

Illustrative compounds of the present invention were tested using this assay protocol and results are presented below in Table A.

TABLE A

| Compound | Wild Type Cell Assay IP (0% NHS) | Wild Type Cell Assay IP (10% NHS) |
|---|---|---|
| 1 | NA | 400 nM |
| 2 | NA | 385 nM |
| 3 | NA | 58 nM |
| 4 | 8 nM | 17 nM |
| 5 | 9 nM | 561 nM |
| 6 | 31 nM | 67 nM |
| 7 | 36 nM | 74 nM |
| 8 | 6 nM | 13 nM |
| 9 | 10 nM | 32 nM |
| 10 | 4 nM | 8 nM |
| 11 | 6 nM | 148 nM |
| 12 | 3 nM | 62 nM |
| 13 | NA | 21 nM |
| 14 | 51 nM | 252 nM |
| 15 | 80 nM | NA |
| 16 | 38 nM | ND |

NA = Not Available

Selected enantiomeric compounds of the present inventions were evaluated in the presence of 100% NHS, and results are presented below in Table B.

TABLE B

| Compound | Wild Type Cell Assay IP (0% NHS) | Wild Type Cell Assay IP (100% NHS) |
|---|---|---|
| 4 | 8 nM | 190 nM |
| 5 (enantiomer of 4) | 9 nM | 5700 nM |
| 10 | 80 nM | 71 nM |
| 11 (enantiomer of 10) | 38 nM | 2803 nM |
| 15 | 80 nM | 56 nM |
| 16 (enantiomer of 15) | 38 nM | 2700 nM |

Uses of the Fused Tricyclic Heterocycle Derivatives

The Fused Tricyclic Heterocycle Derivatives are useful in human and veterinary medicine for treating or preventing HIV infection in a subject. In one embodiment, the Fused Tricyclic Heterocycle Derivatives can be inhibitors of HIV viral replication. In a specific embodiment, the Fused Tricyclic Heterocycle Derivatives are inhibitors of HIV-1. Accordingly, the Fused Tricyclic Heterocycle Derivatives are useful for treating HIV infections and AIDS. In accordance with the invention, the Fused Tricyclic Heterocycle Derivatives can be administered to a subject in need of treatment or prevention of HIV infection.

Accordingly, in one embodiment, the invention provides methods for treating HIV infection in a subject comprising administering to the subject an effective amount of at least one Fused Tricyclic Heterocycle Derivative or a pharmaceutically acceptable salt thereof. In a specific embodiment, the present invention provides methods for treating AIDS in a subject comprising administering to the subject an effective amount of at least one Fused Tricyclic Heterocycle Derivative or a pharmaceutically acceptable salt thereof.

Treatment or Prevention of HIV Infection

The Fused Tricyclic Heterocycle Derivatives are useful in the inhibition of HIV, the treatment of HIV infection and/or reduction of the likelihood or severity of symptoms of HIV infection and the inhibition of HIV viral replication and/or HIV viral production in a cell-based system. For example, the Fused Tricyclic Heterocycle Derivatives are useful in treating infection by HIV after suspected past exposure to HIV by such means as blood transfusion, exchange of body fluids, bites, accidental needle stick, or exposure to subject blood during surgery or other medical procedures.

In one embodiment, the HIV infection has progressed to AIDS.

Accordingly, in one embodiment, the invention provides methods for treating HIV infection in a subject, the methods comprising administering to the subject an effective amount of at least one Fused Tricyclic Heterocycle Derivative or a pharmaceutically acceptable salt thereof. In a specific embodiment, the amount administered is effective to treat or prevent infection by HIV in the subject. In another specific embodiment, the amount administered is effective to inhibit HIV viral replication and/or viral production in the subject.

The Fused Tricyclic Heterocycle Derivatives are also useful in the preparation and execution of screening assays for antiviral compounds. For example the Fused Tricyclic Heterocycle Derivatives are useful for identifying resistant HIV cell lines harboring mutations, which are excellent screening tools for more powerful antiviral compounds. Furthermore, the Fused Tricyclic Heterocycle Derivatives are useful in establishing or determining the binding site of other antivirals to the HIV Integrase.

Combination Therapy

In another embodiment, the present methods for treating or preventing HIV infection can further comprise the administration of one or more additional therapeutic agents which are not Fused Tricyclic Heterocycle Derivatives.

In one embodiment, the additional therapeutic agent is an antiviral agent.

In another embodiment, the additional therapeutic agent is an immunomodulatory agent, such as an immunosuppressive agent.

Accordingly, in one embodiment, the present invention provides methods for treating a viral infection in a subject, the method comprising administering to the subject: (i) at least one Fused Tricyclic Heterocycle Derivative (which may include two or more different Fused Tricyclic Heterocycle Derivatives), or a pharmaceutically acceptable salt thereof, and (ii) at least one additional therapeutic agent that is other than a Fused Tricyclic Heterocycle Derivative, wherein the amounts administered are together effective to treat or prevent a viral infection.

When administering a combination therapy of the invention to a subject, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a Fused Tricyclic Heterocycle Derivative and an additional therapeutic agent may be present in fixed amounts (dosage amounts) in a single dosage unit (e.g., a capsule, a tablet and the like).

In one embodiment, the at least one Fused Tricyclic Heterocycle Derivative is administered during a time when the additional therapeutic agent(s) exert their prophylactic or therapeutic effect, or vice versa.

In another embodiment, the at least one Fused Tricyclic Heterocycle Derivative and the additional therapeutic agent(s) are administered in doses commonly employed when such agents are used as monotherapy for treating a viral infection.

In another embodiment, the at least one Fused Tricyclic Heterocycle Derivative and the additional therapeutic agent(s) are administered in doses lower than the doses commonly employed when such agents are used as monotherapy for treating a viral infection.

In still another embodiment, the at least one Fused Tricyclic Heterocycle Derivative and the additional therapeutic agent(s) act synergistically and are administered in doses lower than the doses commonly employed when such agents are used as monotherapy for treating a viral infection.

In one embodiment, the at least one Fused Tricyclic Heterocycle Derivative and the additional therapeutic agent(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

Viral infections and virus-related disorders that can be treated or prevented using the combination therapy methods of the present invention include, but are not limited to, those listed above.

In one embodiment, the viral infection is HIV infection.

In another embodiment, the viral infection is AIDS.

The at least one Fused Tricyclic Heterocycle Derivative and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of therapy without reducing the efficacy of therapy.

In one embodiment, the administration of at least one Fused Tricyclic Heterocycle Derivative and the additional therapeutic agent(s) may inhibit the resistance of a viral infection to these agents.

As noted above, the present invention is also directed to use of a compound of Formula I with one or more anti-HIV agents. An "anti-HIV agent" is any agent which is directly or indirectly effective in the inhibition of HIV reverse transcriptase or another enzyme required for HIV replication or infection, the treatment or prophylaxis of HIV infection, and/or the treatment, prophylaxis or delay in the onset or progression of AIDS. It is understood that an anti-HIV agent is effective in treating, preventing, or delaying the onset or progression of HIV infection or AIDS and/or diseases or conditions arising therefrom or associated therewith. For example, the compounds of this invention may be effectively administered, whether at periods of pre-exposure and/or post-exposure, in combination with effective amounts of one or more anti-HIV agents selected from HIV antiviral agents, immunomodulators, antiinfectives, or vaccines useful for treating HIV infection or AIDS. Suitable HIV antivirals for use in combination with the compounds of the present invention include, for example, those listed in Table A as follows:

TABLE A

| Name | Type |
| --- | --- |
| abacavir, ABC, Ziagen ® | nRTI |
| abacavir + lamivudine, Epzicom ® | nRTI |
| abacavir + lamivudine + zidovudine, Trizivir ® | nRTI |
| amprenavir, Agenerase ® | PI |
| atazanavir, Reyataz ® | PI |
| AZT, zidovudine, azidothymidine, Retrovir ® | nRTI |
| CMX-157 | nRTI |
| darunavir, Prezista ® | PI |
| ddC, zalcitabine, dideoxycytidine, Hivid ® | nRTI |
| ddI, didanosine, dideoxyinosine, Videx ® | nRTI |
| ddI (enteric coated), Videx EC ® | nRTI |
| delavirdine, DLV, Rescriptor ® | nnRTI |
| Dolutegravir | PI |
| efavirenz, EFV, Sustiva ®, Stocrin ® | nnRTI |
| efavirenz + emtricitabine + tenofovir DF, Atripla ® | nnRTI + nRTI |
| Elvitegravir | InI |
| emtricitabine, FTC, Emtriva ® | nRTI |
| emtricitabine + tenofovir DF, Truvada ® | nRTI |
| emvirine, Coactinon ® | nnRTI |
| enfuvirtide, Fuzeon ® | FI |
| enteric coated didanosine, Videx EC ® | nRTI |
| etravirine, TMC-125 | nnRTI |
| fosamprenavir calcium, Lexiva ® | PI |
| indinavir, Crixivan ® | PI |
| lamivudine, 3TC, Epivir ® | nRTI |
| lamivudine + zidovudine, Combivir ® | nRTI |
| lopinavir | PI |
| lopinavir + ritonavir, Kaletra ® | PI |
| maraviroc, Selzentry ® | EI |
| nelfinavir, Viracept ® | PI |
| nevirapine, NVP, Viramune ® | nnRTI |
| raltegravir, MK-0518, Isentress ® | InI |
| rilpivirine, TMC-278 | nnRTI |
| Rilpivirine + emtricitabine + tenofovir, Complera | nnRTI + nRTI |
| ritonavir, Norvir ® | PI |
| saquinavir, Invirase ®, Fortovase ® | PI |
| stavudine, d4T, didehydrodeoxythymidine, Zerit ® | nRTI |
| tenofovir DF (DF = disoproxil fumarate), TDF, Viread ® | nRTI |
| tipranavir, Aptivus ® | PI |

EI = entry inhibitor; FI = fusion inhibitor; InI = integrase inhibitor; PI = protease inhibitor; nRTI = nucleoside reverse transcriptase inhibitor; nnRTI = non-nucleoside reverse transcriptase inhibitor. Some of the drugs listed in the table are used in a salt form; e.g., abacavir sulfate, indinavir sulfate, atazanavir sulfate, nelfinavir mesylate.

In one embodiment, the one or more anti-HIV drugs are selected from raltegravir, lamivudine, abacavir, ritonavir, darunavir, atazanavir, emtricitabine, tenofovir, elvitegravir, rilpivirine and lopinavir.

In another embodiment, the compound of formula (I) is used in combination with a single anti-HIV drug which is lamivudine.

In still another embodiment, the compound of formula (I) is used in combination with a single anti-HIV drug which is atazanavir.

In another embodiment, the compound of formula (I) is used in combination with a single anti-HIV drug which is darunavir.

In another embodiment, the compound of formula (I) is used in combination with a single anti-HIV drug which is rilpivirine.

In one embodiment, the compound of formula (I) is used in combination with two anti-HIV drugs which are lamivudine and abacavir.

In another embodiment, the compound of formula (I) is used in combination with two anti-HIV drugs which are emtricitabine and tenofovir.

In another embodiment, the compound of formula (I) is used in combination with two anti-HIV drugs which are ritonavir and lopinavir.

In one embodiment, the present invention provides pharmaceutical compositions comprising (i) a compound of formula (I) or a pharmaceutically acceptable salt thereof; (ii) a pharmaceutically acceptable carrier; and (iii) one or more additional anti-HIV agents selected from lamivudine, abacavir, ritonavir and lopinavir, or a pharmaceutically acceptable salt thereof, wherein the amounts present of components (i) and (iii) are together effective for the treatment or prophylaxis of infection by HIV or for the treatment, prophylaxis, or delay in the onset or progression of AIDS in the subject in need thereof.

In another embodiment, the present invention provides a method for the treatment or prophylaxis of infection by HIV or for the treatment, prophylaxis, or delay in the onset or progression of AIDS in a subject in need thereof, which comprises administering to the subject (i) a compound of formula (I) or a pharmaceutically acceptable salt thereof and (ii) one or more additional anti-HIV agents selected from lamivudine, abacavir, ritonavir and lopinavir, or a pharmaceutically acceptable salt thereof, wherein the amounts administered of components (i) and (ii) are together effective for the treatment or prophylaxis of infection by HIV or for the treatment, prophylaxis, or delay in the onset or progression of AIDS in the subject in need thereof.

It is understood that the scope of combinations of the compounds of this invention with anti-HIV agents is not limited to the HIV antivirals listed in Table A, but includes in principle any combination with any pharmaceutical composition useful for the treatment or prophylaxis of AIDS. The HIV antiviral agents and other agents will typically be employed in these combinations in their conventional dosage ranges and regimens as reported in the art, including, for example, the dosages described in the *Physicians' Desk Reference*, Thomson PDR, Thomson PDR, 57$^{th}$ edition (2003), the 58$^{th}$ edition (2004), the 59$^{th}$ edition (2005), and the like. The dosage ranges for a compound of the invention in these combinations are the same as those set forth above.

The compounds of this invention are also useful in the preparation and execution of screening assays for antiviral compounds. For example, the compounds of this invention are useful for isolating enzyme mutants, which are excellent screening tools for more powerful antiviral compounds.

Furthermore, the compounds of this invention are useful in establishing or determining the binding site of other antivirals to HIV integrase, e.g., by competitive inhibition. Thus the compounds of this invention are commercial products to be sold for these purposes.

The doses and dosage regimen of the other agents used in the combination therapies of the present invention for the treatment or prevention of HIV infection can be determined by the attending clinician, taking into consideration the approved doses and dosage regimen in the package insert; the age, sex and general health of the subject; and the type and severity of the viral infection or related disease or disorder. When administered in combination, the Fused Tricyclic Heterocycle Derivative(s) and the other agent(s) can be administered simultaneously (i.e., in the same composition or in separate compositions one right after the other) or sequentially. This particularly useful when the components of the combination are given on different dosing schedules, e.g., one component is administered once daily and another component is administered every six hours, or when the pharmaceutical compositions are different, e.g., one is a tablet and one is a capsule. A kit comprising the separate dosage forms is therefore advantageous.

Compositions and Administration

When administered to a subject, the Fused Tricyclic Heterocycle Derivatives can be administered as a component of a composition that comprises a pharmaceutically acceptable carrier or vehicle. The present invention provides pharmaceutical compositions comprising an effective amount of at least one Fused Tricyclic Heterocycle Derivative and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Additionally, the compositions of the present invention may be formulated in sustained release form to provide the rate controlled release of any one or more of the components or active ingredients to optimize therapeutic effects, i.e., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more Fused Tricyclic Heterocycle Derivatives are administered orally.

In another embodiment, the one or more Fused Tricyclic Heterocycle Derivatives are administered intravenously.

In one embodiment, a pharmaceutical preparation comprising at least one Fused Tricyclic Heterocycle Derivative is in unit dosage form. In such form, the preparation is subdivided into unit doses containing effective amounts of the active components.

Compositions can be prepared according to conventional mixing, granulating or coating methods, respectively, and the present compositions can contain, in one embodiment, from about 0.1% to about 99% of the Fused Tricyclic Heterocycle Derivative(s) by weight or volume. In various embodiments, the present compositions can contain, in one embodiment, from about 1% to about 70% or from about 5% to about 60% of the Fused Tricyclic Heterocycle Derivative (s) by weight or volume.

The compounds of Formula I can be administered orally in a dosage range of 0.001 to 1000 mg/kg of mammal (e.g., human) body weight per day in a single dose or in divided doses. One dosage range is 0.01 to 500 mg/kg body weight per day orally in a single dose or in divided doses. Another dosage range is 0.1 to 100 mg/kg body weight per day orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the subject to be treated. The specific dose level and frequency of dosage for any particular subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The amount and frequency of administration of the Fused Tricyclic Heterocycle Derivatives will be regulated according to the judgment of the attending clinician considering such factors as age, condition and size of the subject as well as severity of the symptoms being treated. The compositions of the invention can further comprise one or more additional therapeutic agents, selected from those listed above herein. Accordingly, in one embodiment, the present invention provides compositions comprising: (i) at least one Fused Tricyclic Heterocycle Derivative or a pharmaceutically acceptable salt thereof; (ii) one or more additional therapeutic agents that are not a Fused Tricyclic Heterocycle Derivative; and (iii) a pharmaceutically acceptable carrier, wherein the amounts in the composition are together effective to treat HIV infection.

Kits

In one aspect, the present invention provides a kit comprising a therapeutically effective amount of at least one Fused Tricyclic Heterocycle Derivative, or a pharmaceutically acceptable salt or prodrug of said compound and a pharmaceutically acceptable carrier, vehicle or diluent.

In another aspect the present invention provides a kit comprising an amount of at least one Fused Tricyclic Heterocycle Derivative, or a pharmaceutically acceptable salt or prodrug of said compound and an amount of at least one additional therapeutic agent listed above, wherein the amounts of the two or more active ingredients result in a desired therapeutic effect. In one embodiment, the one or more Fused Tricyclic Heterocycle Derivatives and the one or more additional therapeutic agents are provided in the same container. In one embodiment, the one or more Fused Tricyclic Heterocycle Derivatives and the one or more additional therapeutic agents are provided in separate containers.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

What is claimed is:
1. A compound having the formula:

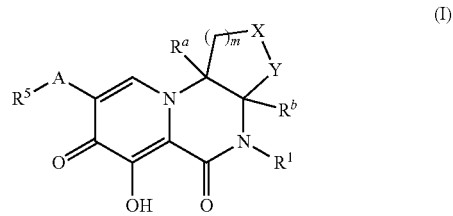

or a pharmaceutically acceptable salts thereof, wherein:
- A is C₁-C₄ alkylene, C₂-C₄ alkenylene, C₃-C₇ cycloalkyl, 5 or 6-membered monocyclic heteroaryl, 4 to 7-membered heterocycloalkyl, arylene, —O—, —NH—C(O)—, —C(O)NH— or —C(O)—;
- the group —X—Y— is selected from —O—C(R²)₂—, —O—C(R²)₂—C(R²)₂—, —C(R²)₂—O—, —N(R⁴)—C(R²)₂—, —N(R⁴)—C(R²)₂—C(R²)₂— and —C(R²)₂—N(R⁴)—;
- m is 1 or 2;
- each occurrence of n is independently 0 or 1;
- Rᵃ is H or C₁-C₆ alkyl;
- Rᵇ is H or C₁-C₆ alkyl;
- R¹ is H or C₁-C₆ alkyl, which is optionally substituted with up to three R³ groups;
- each occurrence of R² is independently selected from H, C₁-C₆ alkyl, C₃-C₇ cycloalkyl, halo, C₁-C₆ haloalkyl, —C(O)R⁶, —C(O)N(R⁶)₂ and —NHC(O)R⁶;
- each occurrence of R³ is independently selected from C₃-C₇ cycloalkyl, 5 or 6-membered monocyclic heteroaryl, 4 to 6-membered monocyclic heterocycloalkyl, C₆-C₁₀ aryl, halo, C₁-C₆ haloalkyl, —OR⁶, —N(R⁶)₂, —C(O)R⁶, —C(O)N(R⁶)₂, —NHC(O)R⁶ and —SR⁶, wherein said C₃-C₇ cycloalkyl group, said 5 or 6-membered monocyclic heteroaryl group, said 4 to 6-membered monocyclic heterocycloalkyl group and said C₆-C₁₀ aryl group can each be optionally and independently substituted with one or more groups, each independently selected from C₁-C₆ alkyl, C₃-C₇ cycloalkyl, 5 or 6-membered monocyclic heteroaryl, 4 to 6-membered monocyclic heterocycloalkyl, C₆-C₁₀ aryl, halo, C₁-C₆ haloalkyl, —OR⁶, —N(R⁶)₂, —C(O)R⁶, —C(O)OR⁶, —C(O)N(R⁶)₂, —NHC(O)R⁶ and —SR⁶;
- R⁴ is C₁-C₆ alkyl, C₃-C₇ cycloalkyl or C₆-C₁₀ aryl, wherein said C₃-C₇ cycloalkyl group and said C₆-C₁₀ aryl group can be optionally substituted with one or more groups, each independently selected from C₁-C₆ alkyl, C₃-C₇ cycloalkyl, C₆-C₁₀ aryl, halo, C₁-C₆ haloalkyl, —C(O)R⁶, —C(O)OR⁶, —C(O)N(R⁶)₂, —NHC(O)R⁶ and —S(O)₂R⁶;
- R⁵ is selected from C₁-C₆ alkyl, —(C₁-C₃ alkylene)ₙ-(C₃-C₇ cycloalkyl), —(C₁-C₃ alkylene)ₙ-(5 or 6-membered monocyclic heteroaryl), —(C₁-C₃ alkylene)ₙ-(4 to 6-membered monocyclic heterocycloalkyl) and —(C₁-C₃ alkylene)ₙ-(C₆-C₁₀ aryl), wherein said C₃-C₇ cycloalkyl group, said 5 or 6-membered monocyclic heteroaryl group, said 4 to 6-membered monocyclic heterocycloalkyl group and said C₆-C₁₀ aryl group can each be optionally and independently substituted with one or more groups, each independently selected from C₁-C₆ alkyl, C₃-C₇ cycloalkyl, 5 or 6-membered monocyclic heteroaryl, 4 to 6-membered monocyclic heterocycloalkyl, C₆-C₁₀ aryl, halo, C₁-C₆ haloalkyl, —OR⁶, —N(R⁶)₂, —C(O)R⁶, —C(O)N(R⁶)₂, —NHC(O)R⁶, —S(O)₂R⁶ and —SR⁶; and
- each occurrence of R⁶ is independently selected from H, C₁-C₆ alkyl, C₃-C₇ cycloalkyl, C₆-C₁₀ aryl and benzyl.

2. The compound of claim 1, wherein R¹ is C₁-C₆ alkyl or (C₁-C₃ alkylene)-O—(C₁-C₆ alkyl), or a pharmaceutically acceptable salt thereof.

3. The compound of claim 1, wherein R⁵ is —(C₁-C₃ alkylene)ₙ-(C₆-C₁₀ aryl), and wherein the C₆-C₁₀ aryl moiety of said —(C₁-C₃ alkylene)ₙ-(C₆-C₁₀ aryl) group can be optionally and independently substituted with up to 3 groups, each independently selected from C₁-C₆ alkyl and halo, or a pharmaceutically acceptable salt thereof.

4. The compound of claim 1, wherein the group —X—Y— is selected from —O—CH₂—, —O—CH₂—CH₂— and —CH₂—O—, or a pharmaceutically acceptable salt thereof.

5. The compound of claim 1, wherein A is 5 or 6-membered monocyclic heteroaryl or —NH—C(O)—, or a pharmaceutically acceptable salt thereof.

6. The compound of claim 1, wherein each occurrence of R² is H, or a pharmaceutically acceptable salt thereof.

7. The compound of claim 1, having the formula (Ia):

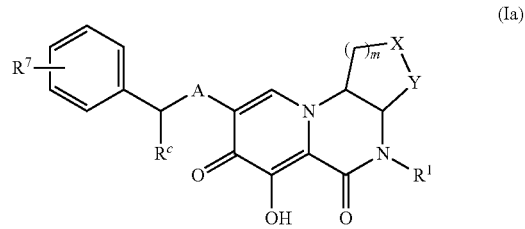

(Ia)

or a pharmaceutically acceptable salts thereof,
wherein:
- A is —NH—C(O)— or 5-membered heteroaryl;
- the group —X—Y— is selected from —O—CH₂—, —O—CH₂—CH₂— and —CH₂—O—;
- m is 1 or 2;
- R¹ is H, C₁-C₆ alkyl or —(C₁-C₃ alkylene)-O—(C₁-C₆ alkyl);
- R⁷ represents up to 2 phenyl group substituents, each independently selected from halo; and
- Rᶜ is H or C₁-C₆ alkyl.

8. The compound of claim 7, wherein m is 1 and the group —X—Y— is —O—CH₂—, or a pharmaceutically acceptable salt thereof.

9. The compound of claim 7, wherein R¹ is H, ethyl, isopropyl, n-propyl or —CH₂CH₂OCH₃, or a pharmaceutically acceptable salt thereof.

10. The compound of claim 1, wherein A is —NHC(O)—, thiadiazolyl or trizolyl, or a pharmaceutically acceptable salt thereof.

11. The compound of claim 7, wherein each occurrence of R⁷ is F, or a pharmaceutically acceptable salt thereof.

12. The compound of claim 7, wherein R⁷ represents two F substitutents, located at the ortho and para positions on the phenyl group to which they are attached, or a pharmaceutically acceptable salt thereof.

13. A compound having the structure:

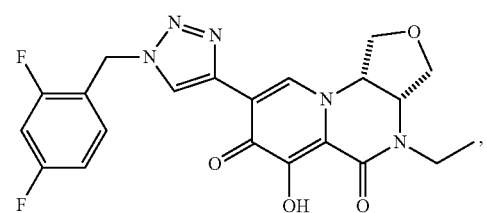

71
-continued
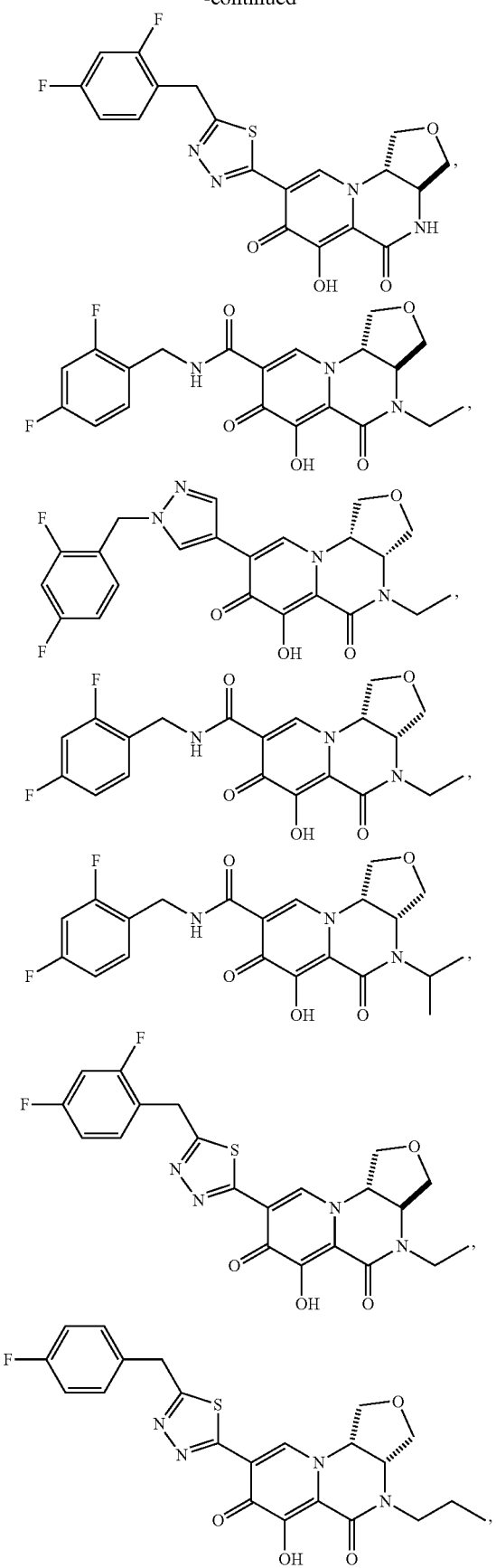
72
-continued
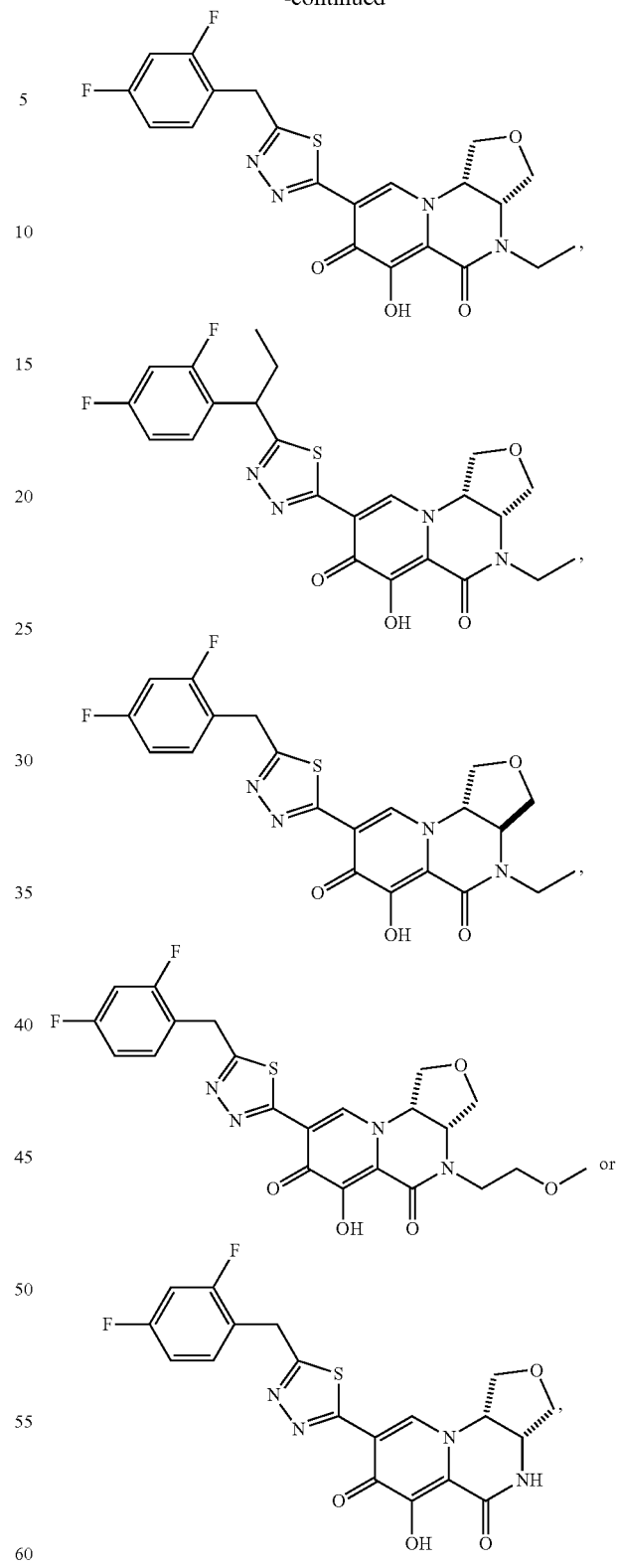
or a pharmaceutically acceptable salt thereof.
14. A pharmaceutical composition comprising an effective amount of a compound according to claim 1, or a pharmaceutically acceptable salt thereof, and a pharmaceutically acceptable carrier.

15. A method for the inhibition of HIV integrase in a subject in need thereof which comprises administering to the subject an effective amount of the compound according to claim 1, or a pharmaceutically acceptable salt thereof.

16. A method for the treatment of infection by HIV or for the treatment, or delay in the onset or progression of AIDS in a subject in need thereof, which comprises administering to the subject an effective amount of the compound according to claim 1, or a pharmaceutically acceptable salt thereof.

17. The pharmaceutical composition of claim 14, further comprising one or more additional therapeutic agents selected from lamivudine, abacavir, darunavir, ritonavir, azanavir, emtricitabine, tenofovir, rilpivirine and lopinavir.

18. A method for the treatment of infection by HIV or for the treatment, or delay in the onset or progression of AIDS in a subject in need thereof, which comprises administering to the subject an effective amount of the compound according to claim 1, or a pharmaceutically acceptable salt thereof, and one or more additional therapeutic agents selected from: lamivudine, darunavir, abacavir, ritonavir, azanavir, emtricitabine, tenofovir, rilpivirine and lopinavir, wherein the amounts administered of the compound of claim 1 and the one or more additional therapeutic agents, are together effective to treat infection by HIV or to treat, prevent or delay the onset or progression of AIDS.

* * * * *